US011629121B2

(12) United States Patent
Park et al.

(10) Patent No.: US 11,629,121 B2
(45) Date of Patent: Apr. 18, 2023

(54) BENZYLIDENEACETONE DERIVATIVE AND USE THEREOF

(71) Applicants: KORPHARM CO., LTD., Goyang-si (KR); GYEONGGIDO BUSINESS & SCIENCE ACCELERATOR, Suwon-si (KR); KOREA UNIVERSITY RESEARCH AND BUSINESS FOUNDATION, Seoul (KR)

(72) Inventors: Gil Hong Park, Goyang-si (KR); Jin Mo Ku, Suwon-si (KR); Jung Hun Lee, Suwon-si (KR); Da Woon Song, Suwon-si (KR); Serk In Park, Seoul (KR); Han Kyeom Kim, Seoul (KR); Soon Hyuck Lee, Seoul (KR); Hong Kyu Kim, Seoul (KR); Pativada Triveni, Seoul (KR); Myung Hwan Kim, Seoul (KR)

(73) Assignees: KORPHARM CO., LTD., Goyang-si (KR); GYEONGGIDO BUSINESS & SCIENCE ACCELERATOR, Suwon-si (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 229 days.

(21) Appl. No.: 16/620,847

(22) PCT Filed: Jul. 27, 2018

(86) PCT No.: PCT/KR2018/008531
§ 371 (c)(1),
(2) Date: Dec. 9, 2019

(87) PCT Pub. No.: WO2019/022556
PCT Pub. Date: Jan. 31, 2019

(65) Prior Publication Data
US 2021/0139414 A1 May 13, 2021

(30) Foreign Application Priority Data

Jul. 27, 2017 (KR) .................. 10-2017-0095699
Aug. 7, 2017 (KR) .................. 10-2017-0099768

(51) Int. Cl.
| | |
|---|---|
| *C07C 235/34* | (2006.01) |
| *A23L 33/10* | (2016.01) |
| *A23L 33/00* | (2016.01) |
| *A61P 19/08* | (2006.01) |
| *A61P 35/00* | (2006.01) |
| *C07C 49/248* | (2006.01) |
| *C07C 49/255* | (2006.01) |

(52) U.S. Cl.
CPC ............ *C07C 235/34* (2013.01); *A23L 33/10* (2016.08); *A23L 33/40* (2016.08); *A61P 19/08* (2018.01); *A61P 35/00* (2018.01); *C07C 49/248* (2013.01); *C07C 49/255* (2013.01); *A23V 2002/00* (2013.01)

(58) Field of Classification Search
CPC ... C07C 49/248; C07C 235/34; C07C 323/22; C07C 49/217; C07C 49/223; C07C 49/255; A23L 33/10; A23L 33/40; A23V 2002/00; A23V 2200/306; A23V 2200/308; A61P 19/08; A61P 35/00; C07D 211/46; C07D 295/10
See application file for complete search history.

(56) References Cited

U.S. PATENT DOCUMENTS

2004/0242659 A1    12/2004   Tasaka et al.

FOREIGN PATENT DOCUMENTS

| EP | 1661898 A1 | 5/2006 |
| KR | 20130100574 A | 9/2013 |
| WO | WO 2004/018462 A1 | 3/2004 |

OTHER PUBLICATIONS

Kamatou et al., Molecules 2012, 17, 6953-6981 (Year: 2012).*
Lyu et al., Food Sci. Biotechnology. vol. 17, No. 6, pp. 1214-1220 (2008) (Year: 2008).*
Ahmad, et al. Scientific World Journal. Published online May 27, 2015. (Year: 2015).*
Patani et al. Scientific World Journal. Published online May 27, 2015. (Year: 2015).*
Motohashi et al., "Inhibitory effects of dehydrozingerone and related compounds on 12-O-tetradecanoylphorbol-13-acetate induced Epstein-Barr virus early antigen activation", Cancer Letters, 1998, 134: 37-42.
Tatsuzaki et al., "Dehydrozingerone, Chalcone, and Isoeugenol Analogues as in Vitro Anticancer Agents", Journal of Natural Products, 2006, 69(10): 1445-1449.
Chemical Abstract Compound, STN express. RN 1704417-22-0, May 14, 2015.
Chemical Abstract Compound, STN express. RN 1824819-50-2, Dec. 8, 2015.
Chemical Abstract Compound, STN express. RN 1706521-81-4, May 18, 2015.
Katsori et al., "Chaicones in Cancer: Understanding their Role in Terms of QSAR", Current Medicinal Chemistry, 2009, 16: 1062-1081.
Kiran et al., "Synthesis, Characterization and Biological Screening of Ferulic Acid Derivatives", Journal of Cancer Therapy, 2015, 6: 917-931.
Rosa et al., "Anticancer Properties of Phenolic Acids in Colon Cancer—A Review", Journal of Nutrition & Food Sciences, 2016, 6:2, 7 pages.
Pativada et al., "Benzylideneacetone Derivatives Inhibit Osteoclastogenesis and Activate Osteoblastogenesis Independently Based on Specific Structure-Activity Relationship", Journal of Medicinal Chemistry, 2019, 62: 6063-6082.

* cited by examiner

*Primary Examiner* — Jean P Cornet
(74) *Attorney, Agent, or Firm* — James S. Keddie; Bozicevic, Field & Francis LLP

(57) ABSTRACT

The present invention relates to novel benzylideneacetone derivatives or uses thereof, more specifically, the present invention relates to a pharmaceutical composition for preventing or treating, or food composition for ameliorating a cancer or a bone disease comprising a compound defined by Formula 1 or pharmaceutically acceptable salt thereof as an active ingredient.

2 Claims, 8 Drawing Sheets

FIG. 8

| Compounds | TRAP IC$_{50}$ (μM) |
|---|---|
| Osmundacetone | 8 |
| KP2 | 3 |
| KP3 | 25 |
| KP4 | 10 |
| KP5 | 0.1 |
| KP6 | 6 |
| KP7 | 8 |
| KP8 | 50 |
| Fosamax | 4 | differentiation

BENZYLIDENEACETONE DERIVATIVE AND USE THEREOF

CROSS-REFERENCE TO RELATED APPLICATIONS

This application is a § 371 national phase of International Application No. PCT/KR2018/008531, filed on Jul. 27, 2018, which claims the benefit of Korean Patent Application Nos. 10-2017-0095699, filed on Jul. 27, 2017, and 10-2017-0099768, filed on Aug. 7, 2017, which applications are incorporated by reference herein.

TECHNICAL FIELD

The present invention relates to novel benzylideneacetone derivatives or uses thereof, more specifically, the present invention relates to a pharmaceutical composition for preventing or treating, or food composition for ameliorating a cancer or bone disease comprising a compound defined by Formula 1 or pharmaceutically acceptable salt thereof as an active ingredient.

BACKGROUND ART

The present application claims priority from and the benefit of Korean Patent Application No. 10-2017-0095699 filed on Jul. 27, 2017, and Korean Patent Application No. 10-2017-0099768 filed on Aug. 7, 2017, which are hereby incorporated by references for all purposes as if fully set forth herein.

Cancer is the leading cause of death as a graying society comes. With the development of surgical surgery, chemotherapy, and radiation therapy, the cure rate is over 70% for all types of cancer, both early and late. However, due to the technical limitations of surgical procedures, and the limitation of dosage due to side effects of chemotherapy and radiation therapy, it is difficult to cure and have high mortality in terminal cancer, metastatic cancer and recurring cancer. In addition, the number of patients who are unable to receive chemotherapy due to the expression of resistance to existing anticancer drugs is increasing.

Therefore, there is an urgent need for the development of a new anticancer agent that has stronger therapeutic effect, that cause low side effects and is safe thereby that can increase the cancer cure rate at high dose, and that has a therapeutic effect even in patients with resistance to existing anticancer drugs.

Bones play an important role in shaping the body's skeletal structure and maintaining blood calcium (Ca2+) levels. Bone is maintained through the balance of the bone remodeling cycle between osteoclasts and osteoblasts that metabolize bone. When the balance between absorption and production of bone is broken down and the amount of absorption is greater than the production amount, various bone-related diseases occur. Representative diseases associated with the differentiation and activation of osteoclasts include osteoporosis, rheumatoid arthritis, arthralgia, Paget's disease, metastatic bone cancer and fractures (Kim J H and Kim N, 2016; Shiozawa Y et al., 2011; Singer F R, 2016).

Rheumatoid arthritis is an autoimmune disease in which autoimmune antibodies promote osteoclast differentiation. The resulting excessive bone absorption exacerbates rheumatoid arthritis (Takayanagi H, 2007). The mechanism is as follows. NFAT transcription factors (NFATc1/c2/c3/c4), which are pivotal transcription factors related to osteoclast differentiation, are basically activated by calcium/calmodulin signaling (Takayanagi H et al., 2002). For full activation, tyrosine-based activation motif (ITAM)-bearing molecules, such as the immunomodulatory proteins DNAX-activating protein 12 (DAP12) and the immune antibody Fc receptor common γ chain (FcRγ), stimulate calcium signaling in immune cells (Pitcher L A and van Oers N S, 2003). In osteoclasts, DAP12 and FcRγ also activate NFATc1 through calcium signaling. Thus, immunoglobulin-like receptors associated with DAP12 and FcRγ play an important role in osteoclast differentiation (Koga T et al., 2004; MoA et al., 2004). In other words, FcRγ interacts with osteoclast-associated receptor (OSCAR) and paired immunoglobulin-like receptor (PIR-A) in osteoclasts. Phosphorylation of ITAM activates phospholipase C γ (PLCγ), which releases intracellular calcium, which activates calcineurin, a calmodulin-dependent phosphatase. Calcineurin directly dephosphorylates NFATc1 serine thereby sending into nucleus and activates. As a result, immune antibodies promote osteoclast differentiation, and excessive bone uptake by osteoclasts exacerbates rheumatoid arthritis. As a result, inhibition of osteoclast differentiation in rheumatoid arthritis patients does not correct the abnormalities of autoimmune mechanisms itself, but it can cure skeletal symptoms such as arthritis and pain.

Paget's disease (Osteitis deformans) is also caused by abnormal bone absorption of osteoclasts (Singer F R, 2016). Then, abnormal bone formation of osteoblasts progresses and this process is repeated, resulting in bone malformation and resulting pain, headache, hearing loss, and the like. It occurs well in arms, legs, pelvis, spine and skull. Newly formed bones are weak and have a high frequency of fractures. Hypercalcemia, heart failure, and incapacitation may be caused (Ralstone S H, 2016). The cause of the disease is unknown, but genetic predisposition and childhood viral infections are suspected to be the cause. Medication can help to control the progression of the disease. Currently the most used therapeutic agents are osteoclast differentiation inhibitor Fosamax and calcitonin to regulate bone metabolism. However, as a side effect, Fosamax has limited long-term use in some patients. If the pain is severe, use Acetaminophen (Tylenol) or nonsteroidal anti-inflammatory drugs (NSAIDs).

Osteoclasts also promote bone metastasis of solid tumors. Bones are the most common site of cancer metastasis. Cancer metastasis to bone causes severe pain and bone breakage, which significantly reduces the likelihood of cure (Weilbaecher K N et al., 2011). Systemic cancer cells are found at the site of blood stem cell proliferation in the bone marrow (Shiozawa Y et al., 2013). Cancer cells significantly promote the differentiation of osteoclasts from bone marrow cells, leading to bone destruction, thereby promoting bone metastasis and cancer growth. Therefore, osteoclasts play a key role in bone metastasis of cancer and inhibit osteoclast differentiation, thereby reducing bone metastasis. Many solid cancer metastases are bone metastases, and cancer cell drives blood stem cells and proliferates based on the location of blood stem cell proliferation, and re-enter into blood stream causing other metastases. The most common cancer of bone metastasis is prostate cancer, where bone metastasis worsens the cancer, making it harder to cure and is the leading cause of death. A direct primary target of human prostate cancer cells also is places of blood stem cell proliferation which serve as a base for metastatic cancer (Shiozawa Y et al., 2011). Osteoclasts also promote cancer growth by promoting blood vessel formation in prostate cancer tissues (Bruni-Cardoso A et al., 2010). Breast cancer cells also promote osteoclast differentiation, and osteoclasts promote cancer recurrence through bone metastasis in breast cancer patients undergoing mastectomy (Danilin S et al., 2012; Lu X et al., 2011).

Bone-targeted therapeutics to prevent bone metastases are currently used clinically, and osteoclasts are main target for anti-cancer drug developments because osteoclasts are one of the key mechanisms for cancer metastasis. Accordingly, the only bisphosphonate-based drug currently approved by the US FDA for the purpose of inhibiting osteoclast differentiation is Zoledronic acid (El-Amm J et al., 2013). Zoledronic acid preserves bones and increases survival rates. Zoledronic acid significantly reduced bone metastasis in high risk nonmetastatic prostate cancer (Wirth M et al., 2014). The administration of Zoledronic acid with parathyroid hormone, a bone production stimulator, further reduced bone metastasis (Schneider A et al., 2005). Denosumab, a monoclonal antibody to RANKL, a signaling agent for osteoclast differentiation, also inhibits bone metastasis in prostate cancer, demonstrating that osteoclast inhibition is important for inhibiting bone metastasis in cancer (Smith M R et al., 2012). In patients with multiple myeloma, the administration of Zoledronic acid inhibits osteoclast differentiation and significantly inhibits bone metastasis (Zhuang J et al., 2012).

Osteoporosis is triggered by activation of osteoclasts, which disrupts the balance between bone uptake and production, resulting in greater absorption than production. Osteoporosis reduces the density of bone parenchyma and increases the frequency of fractures. It occurs most frequently in women whose hormone balance is compromised, such as middle-aged and older women, and also in patients who are unable to move due to fractures or severe diseases. In recent years, the incidence has also increased in older men.

In the molecular mechanism by which bone marrow monocyte/macrophage lineage cells differentiate into osteoclasts, the following two cytokines play an important role (Teitelbaum S L and Ross F P, 2003). (i) When the macrophage colony-stimulating factor (M-CSF) binds to its receptor, c-Fms, osteoclast progenitor cells proliferate and survive. Binding of the receptor activator of nuclear factor-KB ligand (RANKL) to its receptor RANK activates osteoclast differentiation and bone absorption and allows mature osteoclasts to survive (Lacey D L et al., 1998; Lum L et al., 1999; Sherr C J, 1990; Suda T et al., 1999; Wong B R et al., 1999). (ii) When M-CSF induces activation of c-Fms, osteoclast progenitor cells proliferate and survive through the ERK and PI3K/Akt pathways (Mancini et al., 1997). (iii) RANKL (OPGL, ODF, TRANCE) and RANK also regulate osteoclast formation and function (Anderson D M et al., 1997; Dougall W C et al., 1999; Kong Y Y et al., 1999). When RANKL binds to RANK, TNF receptor-associated factors (TRAFs) such as TRAFs 1, 2, 3, 5, and 6 bind RANK (Darnay B G et al., 1998; Walsh M C and Choi Y, 2003). OF TRAFs, TRAF6 is the most important for osteoclast formation and function (Lomaga M A et al., 1999; Naito A et al., 1999). TRAF6 delivers RANKL/RANK signals to NF-κB, c-Jun N-terminal kinase (JNK), extracellular signal-regulated kinase (ERK), p38, Akt, Nuclear Factor Of Activated T-Cells 1 (NFATc1), causing cell proliferation, fusion, and differentiation (Kobayashi N et al., 2001; Lomaga M A et al., 1999; Naito A et al., 1999; Takayanagi H et al., 2002; Wong B R et al., 1998; Wong B R et al., 1999)

The existing direction of developing a therapeutic agent for osteoporosis has been to find a substance that can prevent bone loss by inhibiting bone absorption of osteoclasts. The representative drug is Fosamax, a bisphosphonate family. In the same manner, much research has been conducted on the effects of arachidonate metabolites on bone tissue metabolism (Lee Sung-eun, 1999). Leukotriene-B4 (LTB4) is one of the metabolites of the 5-lipoxygenase pathway, a metabolic pathway of arachidonate (Ford-Hutchinson, A. W. et al., 1980). C433, an interstitial cell obtained from giant cell tumors, has been reported to increase the number and activity of osteoblasts by increasing 5-lipoxygenase metabolites (Mundy, G. R. et al., 1993). Increasing bone absorption has been observed when LTB4 is administered during bone tissue culture (Bonewald, L. F. et al., 1996). In vitro and in vivo studies have shown that LTB4 induces bone absorption by increasing the production of osteoclasts (Bonewald, L. F. et al., 1996). Accordingly, many LTB4 receptor antagonists have been developed for the treatment of osteoporosis, but have not been successful in sufficiently inhibiting bone parenchymal uptake of osteoclasts.

In addition, the side effects and expensive medicines of the existing osteoporosis treatments have become a major obstacle to administering in sufficient doses for the treatment of patients. Major side effects of Fosamax include severe esophagitis, kidney damage, liver damage, hypocalcemia, and muscle spasms. Roche Bonviva has side effects such as systemic muscle pain and body aches. Novartis Aclasta (zoledronate) and Eli Lilly's anabolic remedy parathyroid hormones, Forsteo and Forteo (teriparatide), are effective but too expensive to use. In particular, Forsteo/Forteo are not applicable to broad range of patient groups because it cannot be used in patients with metabolic bone diseases such as hypersensitivity patients, pregnant women, breastfeeding, hypercalcemia, renal failure, hyperparathyroidism and Paget's disease; patients with unexplained elevations of alkaline phosphatase; patients with radiation therapy; patients with bone marrow or bone metastases.

Therefore, there is an urgent need to develop therapeutic agents for treating bone-related diseases that are more effective, safe without side effects, and can be produced at lower cost than existing therapeutic agents.

DETAILED DESCRIPTION OF THE INVENTION

Technical Problem

Accordingly, the present inventors have synthesized novel compounds to develop a therapeutic agent for a cancer or bone disease with less side effects, safety, and excellent effects, thereby completed the present invention by confirming that these compounds have effect on anticancer, bone loss inhibition, and osteoblast activity.

Therefore, an aspect of the present invention is to provide a compound defined by Formula 1 below or a pharmaceutically acceptable salt thereof:

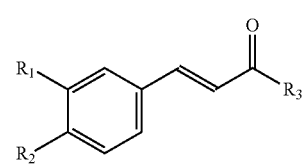

[Formula 1]

wherein, R1 and R2 are different from each other,
R1 and R2 are each independently selected from the group consisting of —H, —OH, —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S;

R3 is one selected from the group consisting of $C_{1-4}$ straight or branched alkyl, —$NH_2$, —NHR4, —$N(R4)_2$, and —OH; and R4 is $C_{1-4}$ straight or branched alkyl.

Another aspect of the present invention is to provide a pharmaceutical composition for preventing or treating a cancer comprising the compound defined by Formula 1 above or the pharmaceutically acceptable salt thereof as an active ingredient.

Still another aspect of the present invention is to provide a pharmaceutical composition for preventing or treating a bone disease comprising the compound defined by Formula 1 above or the pharmaceutically acceptable salt thereof as an active ingredient.

Still another aspect of the present invention is to provide use of a compound defined by Formula 1 above or the pharmaceutically acceptable salt thereof for preparing an agent for treating a cancer.

Still another aspect of the present invention is to provide use of a compound defined by Formula 1 above or the pharmaceutically acceptable salt thereof for preparing an agent for treating a bone disease.

Still another aspect of the present invention is to provide a method for treating a cancer in a subject, the method comprising administering to the subject in need thereof an effective amount of a composition comprising a compound defined by Formula 1 above or the pharmaceutically acceptable salt thereof as an active ingredient.

Still another aspect of the present invention is to provide a method for treating a bone disease in a subject, the method comprising administering to the subject in need thereof an effective amount of a composition comprising a compound defined by Formula 1 above or the pharmaceutically acceptable salt thereof as an active ingredient.

Technical Solution

In accordance with an aspect of the present invention, there is provided a compound defined by Formula 1 below or a pharmaceutically acceptable salt thereof:

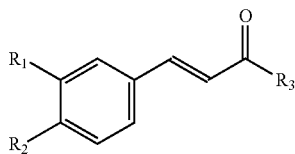

[Formula 1]

wherein, R1 and R2 are different from each other,

R1 and R2 are each independently selected from the group consisting of —H, —OH, —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S;

R3 is one selected from the group consisting of $C_{1-4}$ straight or branched alkyl, —$NH_2$, —NHR4, —$N(R4)_2$, and —OH; and R4 is $C_{1-4}$ straight or branched alkyl.

In accordance with another aspect of the present invention, there is provided a pharmaceutical composition for preventing or treating a cancer comprising the compound defined by Formula 1 above or the pharmaceutically acceptable salt thereof as an active ingredient.

In accordance with another aspect of the present invention, there is provided a pharmaceutical composition for preventing or treating a bone disease comprising the compound defined by Formula 1 above or the pharmaceutically acceptable salt thereof as an active ingredient.

In accordance with another aspect of the present invention, there is provided use of a compound defined by Formula 1 above or the pharmaceutically acceptable salt thereof for preparing an agent for treating a cancer.

In accordance with another aspect of the present invention, there is provided use of a compound defined by Formula 1 above or the pharmaceutically acceptable salt thereof for preparing an agent for treating a bone disease.

In accordance with another aspect of the present invention, there is provided a method for treating a cancer in a subject, the method comprising administering to the subject in need thereof an effective amount of a composition comprising a compound defined by Formula 1 above or the pharmaceutically acceptable salt thereof as an active ingredient.

In accordance with another aspect of the present invention, there is provided a method for treating a bone disease in a subject, the method comprising administering to the subject in need thereof an effective amount of a composition comprising a compound defined by Formula 1 above or the pharmaceutically acceptable salt thereof as an active ingredient.

Hereinafter, the present invention will be described in detail.

The Present Invention Provides a Compound Defined by Formula 1 Below or a Pharmaceutically Acceptable Salt Thereof:

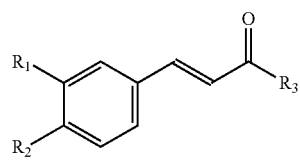

[Formula 1]

wherein, R1 and R2 are different from each other,

R1 and R2 are each independently selected from the group consisting of —H, —OH, —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S;

R3 is one selected from the group consisting of $C_{1-4}$ straight or branched alkyl, —$NH_2$, —NHR4, —$N(R4)_2$, and —OH; and R4 is $C_{1-4}$ straight or branched alkyl.

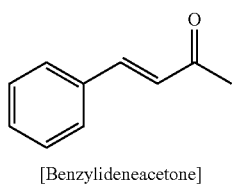

[Benzylideneacetone]

Benzylideneacetone is defined by the molecular formula of $C_{10}H_{10}O$ (molecular weight 146.19 g/mol) and the above structural Formula, and is a compound having the structure of the Formula above. It is also called Benzalacetone, Methyl Styryl ketone, Benzylidene acetone or IUPAC is (E)-4-Phenylbut-3-ene-2-one, and exists as yellow crystals at room temperature.

The novel compounds defined by Formula 1 of the present invention are derivatives of Benzylideneacetone and have the following structure.

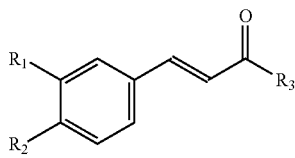

[Formula 1]

wherein, R1 and R2 are different from each other,

R1 and R2 are each independently selected from the group consisting of —H, —OH, —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S;

R3 is one selected from the group consisting of $C_{1-4}$ straight or branched alkyl, —NH₂, —NHR4, —N(R4)₂, and —OH; and R4 is $C_{1-4}$ straight or branched alkyl.

As used herein, the term "alkyl" is used to describe a group or portion of a group comprising a straight or branched alkyl group containing 1 to 4 carbon atoms; Examples of such groups include methyl, ethyl, propyl, isopropyl, n-butyl, isobutyl, tert butyl.

As used herein, the term "alkoxy" means O-alkyl.

The "alkyl" described in the definition of alkoxy is the same as the "alkyl group" used in the present invention, specifically, it is a methoxy group, an ethoxy group, a propoxy group, an isopropoxy group, n-butoxy group, isobutoxy group, t-butoxy group.

As used herein, the term "aryloxy" means O-aryl.

"Aryl" described in the definition of aryloxy is the same as "benzyl group" used in the present invention. Specifically, it includes an unsubstituted aryl group or heteroaryl group containing one or more N, S or O, which is a hetero atom. The aryloxy group containing the unsubstituted aryl group is the same as "benzyloxy" used in the present invention.

In addition, one or more substituents may be independently included as a substituent of the aryl group. In this case, the substituent specifically includes a hydroxy group, an amino group, an alkyl group, an alkoxy group, a carboxylic acid group, a carboxyl ester group, and a carboxyamide group.

As used herein, the term "carboxyl ester group" refers to an ester substituted with an O-alkyl or O-aryl group, and a "carboxyamide group" refers to N-alkyl, N,N-dialkyl, N-aryl, N,N-diaryl.

The aryl group, alkyl group and alkoxy group are as described in the present specification.

As used herein, the term "halogen" refers to a halogen atom, and includes fluorine, chlorine, bromine, iodine, and the like, and R2 halogen of the compound of the present invention may preferably be a fluorine.

In the present invention, "heterocycloalkyl of 3 to 7 atoms having one or more hetero atoms, wherein the hetero atoms consist of O, N and S" may preferably have the following structural formula:

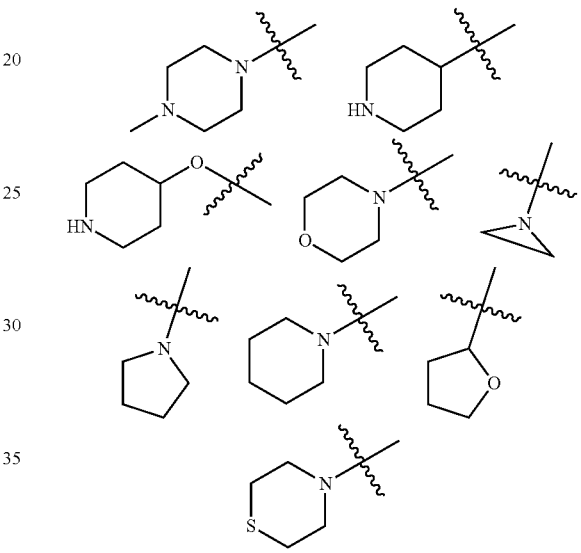

Preferably, the compound defined by Formula 1 of the present invention is a compound, wherein R1 and R2 are different from each other, R1 is one selected from the group consisting of —OH, methyl, methoxy, —F, and —SH;

R2 is one selected from the group consisting of —OH, —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S;

R3 is methyl or —NH₂.

More preferably, the compound defined by Formula 1 of the present invention is a compound, wherein R1 and R2 are different from each other, R1 is one selected from the group consisting of —OH, methyl, methoxy, and —F, R2 is one selected from the group consisting of —OH, methyl, methoxy, and —F, R3 is methyl, or —NH₂.

Even more preferably, the compound defined by Formula 1 of the present invention is selected from the group consisting of the following compounds:

(1) (E)-4-(3-hydroxy-4-methylphenyl)but-3-en-2-one (M.W 176.21; Brown solid)

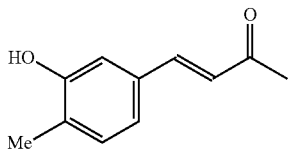

(2) (E)-4-(4-fluoro-3-hydroxyphenyl)but-3-en-2-one (M.W 176.21: brown solid)

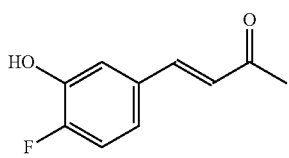

(3) (E)-4-(4-hydroxy-3-methoxyphenyl)-3-buten-2-one (M.W 192.21, white solid)

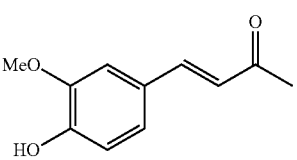

(4) (E)-4-(3-hydroxy-4-methoxyphenyl)-3-buten-2-one (M.W 192.21, yellow solid)

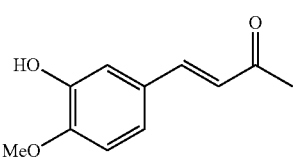

(5) (E)-4-(3-fluoro-4-hydroxyphenyl)-3-buten-2-one (M.W 180.18, yellow solid)

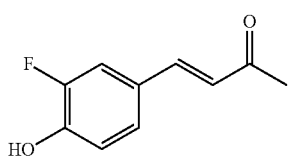

(6) (E)-3-(3-hydroxy-4-methylphenyl)acrylamide (M.W 177.2, yellow solid)

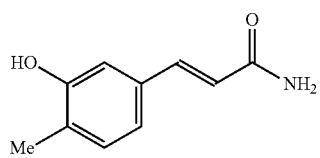 [SMILES: Cc1ccc(/C=C/C(N)=O)cc1O]

(7) (E)-3-(4-fluoro-3-hydroxyphenyl)acrylamide (M.W 181.17, yellow solid)

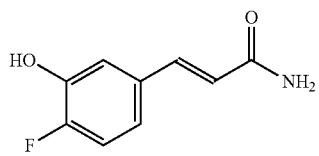 [SMILES: NC(=O)/C=C/c1ccc(F)c(O)c1]

(8) (E)-4-(4-mercapto-3-hydroxyphenyl)but-3-en-2-one

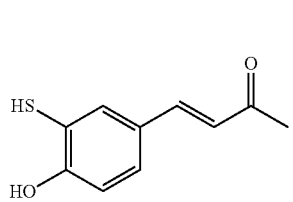

(9) (E)-4-(4-hydroxy-3-mercaptophenyl)but-3-en-2-one

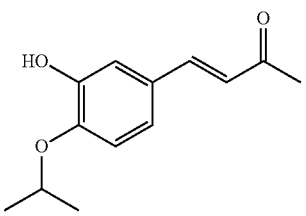 [SMILES: CC(=O)/C=C/c1ccc(OC(C)C)c(O)c1]

(10) (E)-4-(3-hydroxy-4-isopropoxyphenyl)but-3-en-2-one;

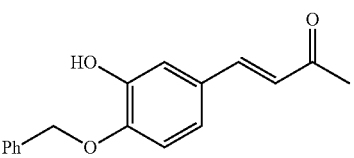 [SMILES: CC(=O)/C=C/c1ccc(OCc2ccccc2)c(O)c1]

(11) (E)-4-(4-(benzyloxy)-3-hydroxyphenyl)but-3-en-2-one

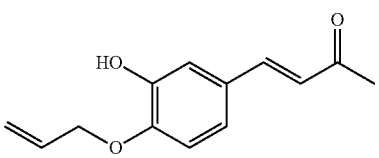 [SMILES: C=CCOc1ccc(/C=C/C(C)=O)cc1O]

(12) (E)-4-(4-(allyloxy)-3-hydroxyphenyl)but-3-en-2-one

(13) (E)-4-(3-hydroxy-4-(4-methylpiperazine-1-yl)phenyl)but-3-en-2-one

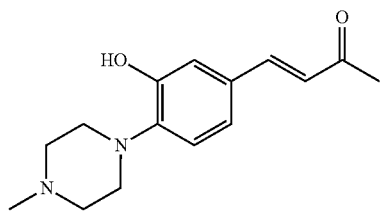 [SMILES: CC(=O)/C=C/c1ccc(N2CCN(C)CC2)c(O)c1]

(14) (E)-4-(3-hydroxy-4-(pyrrolidine-1-yl)phenyl)but-3-en-2-one

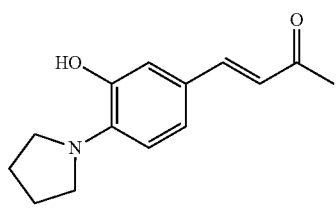 [SMILES: CC(=O)/C=C/c1ccc(N2CCCC2)c(O)c1]

(15) (E)-4-(3-hydroxy-4-(4-hydroxyphenoxy)phenyl)but-3-en-2-one;

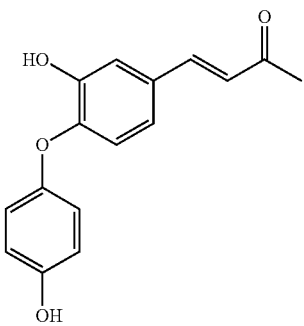 [SMILES: CC(=O)/C=C/c1ccc(Oc2ccc(O)cc2)c(O)c1]

(16) (E)-4-(3-hydroxy-4-(piperidine-4-yloxy)phenyl)but-3-en-2-one.

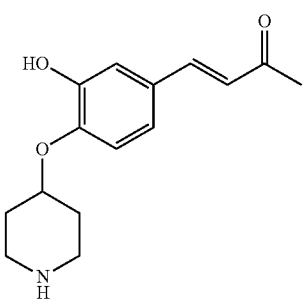 [SMILES: CC(=O)/C=C/c1ccc(OC2CCNCC2)c(O)c1]

The compounds included in the compositions of the present invention can be used on their own or in the form of salts, preferably pharmaceutically acceptable salts. In the present invention, 'pharmaceutically acceptable' refers to a physiologically acceptable and normally does not cause an allergic reaction or a similar reaction when administered to a human, and the salts preferably are acid salts formed by pharmaceutically acceptable free acids. Organic acids and inorganic acids may be used as the free acid. The organic acid is not limited thereto, citric acid, acetic acid, lactic acid, tartaric acid, maleic acid, fumaric acid, formic acid, propionic acid, oxalic acid, trifluoroacetic acid, benzoic acid, gluconic acid, metasulfonic acid, glycolic acid, succinic acid, 4-toluenesulfonic acid, glutamic acid and aspartic acid. In addition, the inorganic acid includes, but is not limited to, hydrochloric acid, bromic acid, sulfuric acid and phosphoric acid.

The compound defined by Formula 1 of the present invention may be naturally isolated or manufactured by a chemical synthesis method of a compound known in the art, a manufacturing method described herein.

The Present Invention Provides a Pharmaceutical Composition for Preventing or Treating a Cancer or Bone Disease Comprising the Compound Defined by Formula 1 Above or the Pharmaceutically Acceptable Salt Thereof as an Active Ingredient.

The compound defined by Formula 1 or a pharmaceutically acceptable salt thereof is as described above in the present specification.

The compound of formula 1 of the present invention is very effective in the treatment of cancer. Such cancer, for example, may be a cancer such as breast cancer, colorectal cancer, lung cancer, small cell lung cancer, gastric cancer, liver cancer, blood cancer, bone cancer, pancreatic cancer, skin cancer, head or neck cancer, skin or eye melanoma, uterine cancer, ovarian cancer, rectal cancer, anal muscle cancer, colon cancer, breast cancer, fallopian tube carcinoma, endometrial carcinoma, cervical cancer, vaginal cancer, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureter cancer, renal cell carcinoma, renal pelvic carcinoma, CNS tumor, primary CNS lymphoma, spinal cord tumor, brainstem glioma and pituitary adenoma, or combination of one or more cancers.

The present inventors confirmed that in one embodiment, the compounds defined by Formula 1 showed strong cytotoxicity to cancer cells but little cytotoxicity to normal cells. Thus, those skilled in the art would be able to anticipate the effects of effective prevention, amelioration or treatment of cancer using the activity of the compounds.

In another embodiment, the present inventors confirmed that the compounds of Formula 1 effectively inhibit the differentiation of osteoclasts, which serve to destroy and reabsorb bone tissue. From the bone marrow cells isolated from the mouse, monocytes, stem cells progenitor cells of osteoclasts, were isolated and stimulated with differentiation-promoting factors, RANKL and M-CSF, and treated with compounds to determine the effects on osteoclast differentiation. As a result, differentiation of bone marrow cells into multinuclear osteoclasts was effectively inhibited.

In addition, the inventors confirmed that the compounds of the present invention significantly inhibit osteoclast differentiation and increase osteoblast differentiation and activity.

Therefore, the present inventors confirmed that the compound defined by Formula (1) has excellent osteoclast differentiation inhibitory activity and osteoblast differentiation activity, as well as very low cytotoxicity and is safe.

Therefore, it can be understood that those skilled in the art can utilize the activities of the compounds to effectively prevent, ameliorate or treat various bone diseases caused by decreased bone density and strength as the balance between bone resorption by osteoclasts, formation of new bone matrix by osteoblasts, and bone metabolism during subsequent mineralization disrupted.

In the present invention, the bone disease may be, for example, but not limited to osteoporosis, Paget's disease, rickets, osteomalacia, nephrotic dystrophy in patients with renal failure, arthralgia, fracture, rheumatoid bone disease, degenerative bone disease, metastatic bone cancer, primary tumors in the bone, periodontal disease, inflammatory alveolar bone disease and inflammatory bone absorption disease, and preferably osteoporosis, Paget's disease, rickets, arthralgia, fracture, rheumatoid bone disease, metastatic bone cancer. For the correlation between each of the above diseases and osteoclasts and osteoblasts, see the background of the art and Examples herein.

As used herein, the term "treatment" refers to a clinical procedure to change the natural process of the individual or cell being treated, and may also be performed for the prevention of clinical pathology. Desirable effects of treatment include reducing the occurrence or recurrence of the disease, alleviating the symptoms, reducing any direct or indirect pathological consequences of the disease, decreasing the rate of disease progression, improving the disease state, improving, alleviating or improving the prognosis, and the like. Include. As used herein, the term "prevention" also means any action that inhibits the onset of a disease or delays the progression of a disease.

The appropriate effective amount and dosage of the pharmaceutical composition of the present invention may be determined by those skilled in the art with consideration of various factors, such as route of administration, time of administration, number of treatments, duration of treatment, age, weight, health condition, sex, severity of disease, sensitivity to drugs, diet and excretion rate. The effective amount refers to an amount sufficient to have an effect of improving, treating, preventing, detecting or diagnosing cancer or bone disease when administered to an individual. The subject may be an animal, preferably an animal including a mammal, most preferably a human, and may be a cell, tissue, organ or the like derived from the animal. The subject may be a patient with a bone disease in need of treatment.

The administration may be administered once or several times a day. The pharmaceutical composition of the present invention may be administered alone or in combination with other therapeutic agents known to be effective in the prevention or treatment of bone disease, and when administered in combination, may be administered sequentially or simultaneously with other therapeutic agents. Dosage of the pharmaceutical composition of the present invention, when administered alone or in combination, is preferably administered in such an amount that the maximum effect can be obtained in a minimum amount without side effects, which can be easily determined by those skilled in the art.

The pharmaceutical composition of the present invention may be formulated in various ways according to the route of administration by a method known in the art together with a pharmaceutically acceptable carrier. Pharmaceutically acceptable means a nontoxic composition which, when administered to humans, does not inhibit the action of the active ingredient and does not usually cause an allergic reaction such as gastrointestinal disorders, dizziness or the like. Such carriers include all kinds of solvents, dispersion media, oil-in-water or water-in-oil emulsions, aqueous compositions, liposomes, microbeads and microsomes.

The route of administration may be administered orally or parenterally. Parenteral methods of administration may be, but are not limited to, intravenous, intramuscular, intraarterial, intramedullary, intradural, intracardiac, transdermal, subcutaneous, intraperitoneal, intranasal, intestinal, topical, sublingual or rectal administration.

In the case of oral administration of the pharmaceutical composition of the present invention, the pharmaceutical composition of the present invention may be powder, granule, tablet, pill, sugarcoated pill, capsule, liquid, gel, syrup, suspension, wafer, and the like according to a method known in the art together with a suitable oral administration carrier. Examples of suitable carriers include sugars, including lactose, dextrose, sucrose, sorbitol, mannitol, xylitol, erythritol and maltitol; starches, including corn starch, wheat starch, rice starch and potato starch; celluloses including cellulose, methyl cellulose, sodium carboxymethylcellulose, hydroxypropylmethylcellulose and the like; fillers such as gelatin, polyvinylpyrrolidone, and the like. In addition, crosslinked polyvinylpyrrolidone, agar, alginic acid or sodium alginate and the like may optionally be added as a disintegrant. Furthermore, the pharmaceutical composition may further include an anticoagulant, a lubricant, a humectant, a perfume, an emulsifier, a preservative, and the like.

In addition, when administered parenterally, the pharmaceutical compositions of the present invention may be formulated according to methods known in the art in the form of injections, transdermal and nasal inhalants with suitable parenteral carriers. Such injections must be sterile and protected from contamination of microorganisms such as bacteria and fungi. Examples of suitable carriers for injections include, but are not limited to, solvents or dispersion media comprising water, ethanol, polyols (e.g., glycerol, propylene glycol and liquid polyethylene glycols, etc.), mixtures thereof and/or vegetable oils. More preferably, suitable carriers may be Hanks' solution, Ringer's solution, phosphate buffered saline (PBS) containing triethanol amine or sterile water for injection, isotonic solution such as 10% ethanol, 40% propylene glycol and 5% dextrose and the like. In order to protect the injection from microbial contamination, various antibacterial and antifungal agents such as parabens, chlorobutanol, phenol, sorbic acid, thimerosal, and the like may be further included. In addition, the injection may in most cases further comprise an isotonic agent, such as sugar or sodium chloride.

In the case of transdermal administration agents, ointments, creams, lotions, gels, external solutions, pastas, linings, air rolls and the like are included. In the above, transdermal administration means that the pharmaceutical composition is topically administered to the skin so that an effective amount of the active ingredient contained in the pharmaceutical composition is delivered into the skin. For example, the pharmaceutical composition of the present invention may be prepared in an injectable formulation and administered by lightly pricking or directly applying the skin with a 30-gauge thin needle. These formulations are described in article, Remington's Pharmaceutical Science, 15th Edition, 1975, Mack Publishing Company, Easton, Pa., a prescription generally known in pharmaceutical chemistry.

In the case of an inhalation dosage form, the compound used in accordance with the present invention may be conveniently delivered in the form of an aerosol spray from a pressurized pack or nebulizer, while using a suitable propellant, such as dichlorofluoromethane, trichlorofluoromethane, dichlorotetrafluoroethane, carbon dioxide and other suitable gas. In the case of a pressurized aerosol, the dosage unit may be determined by providing a valve that delivers a metered amount. For example, gelatin capsules and cartridges used for an inhaler or insufflator may be formulated to contain a compound, and a powder mixture of a suitable powder base such as lactose or starch.

Other pharmaceutically acceptable carriers may be referred to those described in the following references (Remington's Pharmaceutical Sciences, 19th ed., Mack Publishing Company, Easton, Pa., 1995).

In addition, the pharmaceutical compositions according to the present invention may comprise one or more buffers (eg, saline or PBS), carbohydrates (eg, glucose, mannose, sucrose or dextran), antioxidants, bacteriostatic agents, chelating agents (Eg, EDTA or glutathione), adjuvants (eg, aluminum hydroxide), suspending agents, thickening agents, and/or preservatives.

In addition, the pharmaceutical compositions of the present invention may be formulated using methods known in the art to provide rapid, sustained or delayed release of the active ingredient after administration to a mammal.

The Present Invention Provides a Food Composition for Preventing or Ameliorating a Cancer or Bone Disease Comprising the Compound Defined by Formula 1 Above or the Pharmaceutically Acceptable Salt Thereof as an active ingredient.

The effect of preventing or ameliorating a cancer or bone disease of the compound defined by Formula (1) identified by the inventors is as described above in the present specification.

The food composition of the present invention includes all forms of functional foods, nutritional supplements, health foods, food additives and feeds for consumption by humans or animals including livestock. Such types of Food compositions may be prepared in a variety of forms according to conventional methods known in the art.

For example, as a health food, the composition for food itself of the present invention may be prepared in the form of tea, juice and drink for drinking, or granulated, encapsulated and powdered. In addition, the food composition of the present invention may be prepared in the form of a composition by mixing with a known substance or active ingredient known to have the effect of preventing or improving bone diseases.

The food composition of the present invention may be added into beverages (e.g., alcoholic beverages), fruits and processed foods thereof (e.g., canned fruits, bottled jam, and marmalade), fish, meat and processed foods thereof (e.g., ham and corn beef sausage), breads and noodles (e.g., udon, buckwheat noodles, ramen noodles, spaghetti, and macaroni), juice, various drinks, cookies, taffy, dairy product (e.g., butter and cheese), edible vegetable oil, margarine, vegetable protein, retort food, frozen food, and various kinds of seasoning (e.g., soybean paste, soy sauce, and sauce) to prepare the functional food.

The preferred content of the food composition according to the present invention is not limited thereto, but is preferably 0.01 to 50% by weight of the total weight of the finally prepared food. In order to use the food composition of the present invention in the form of a food additive, it may be prepared and used in powder or concentrate form.

The Present Invention Provides a Method for Preparing a Compound Defined by Formula 1.

The compound defined by Formula 1 is prepared under a suitable reaction solvent. Solvents that can be used include methanol, ethanol, propanol, butanol, chloroform, dichloromethane, ethylacetic acid, nucleic acid, benzene, methylene chloride, acetone, tetrahydrofuran (THF), dioxane, DMF or a mixed solvent thereof.

Compounds in which R3 of the compound of Formula 1 of the present invention is a methyl group may be prepared by the following Preparation Method 1 or 3, and compounds having R3 of $-NH_2$ may be prepared by the following Preparation Method 2.

Hereinafter, the preparation method according to the present invention will be described in detail step by step.

Preparation Method 1 (Method 1)

In the present invention, step a is a step of preparing compound 2 by hydrolyzing methyl ether of compound 1 under acid catalyzed conditions.

At this time, $BBr_3$, $AlCl_3$, HBr, and the like can be used as a catalyst. In this case, $CH_3CN$, $CH_2Cl_2$, and the like can be used as the reaction solvent.

Step b below is a step of preparing compound 3 by reacting compound 2 prepared in step a with $CuBr_2$. In step b, an organic solvent such as acetone or DMF can be used as the reaction solvent, and the reaction temperature is preferably at 40° C. to 70° C.

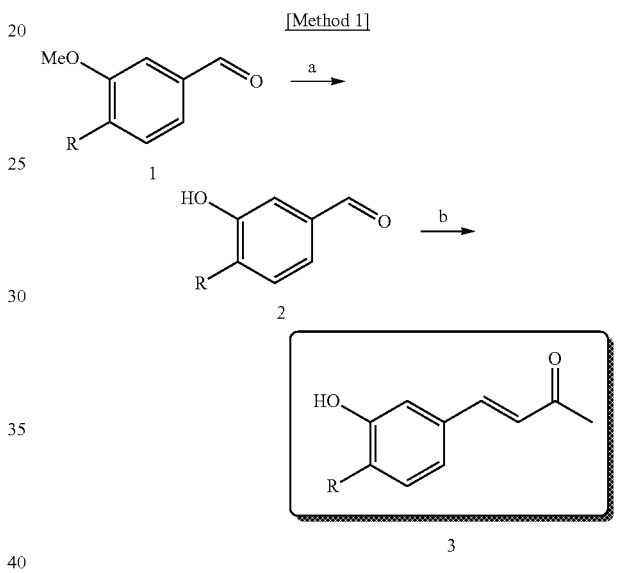

[Method 1]

R in the Method 1 is one selected from the group consisting of —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S.

The alkyl group, alkoxy group, aryloxy, halogen, cycloalkyl and the like are as described above.

Preparation Method 2 (Method 2)

In the present invention, step a' below is a step of preparing compound 2 by reacting compound 1 with triethylphosphonoacetate. At this time, THF, methanol, water and the like can be used as the reaction solvent, and the reaction temperature is preferably room temperature.

Step b' below is a step of preparing compound 3 by reacting methyl ester group of compound 2 with a base. At this time, LiOH, NaOH and the like can be used as a base. In this case, THF, methanol, water and the like can be used as the reaction solvent.

Step c' below is a step of preparing compound 4 by reacting hydroxy group of compound 3 with $NH_4HCO_3$. At this time, dioxane can be used as the reaction solvent.

Step d' below is a step of preparing compound 5 by hydrolyzing methyl ether of compound 4 under acid catalysis conditions.

At this time, $BBr_3$, $AlCl_3$, HBr, and the like can be used as a catalyst. In this case, $CH_3CN$, $CH_2Cl_2$, and the like can be used as the reaction solvent.

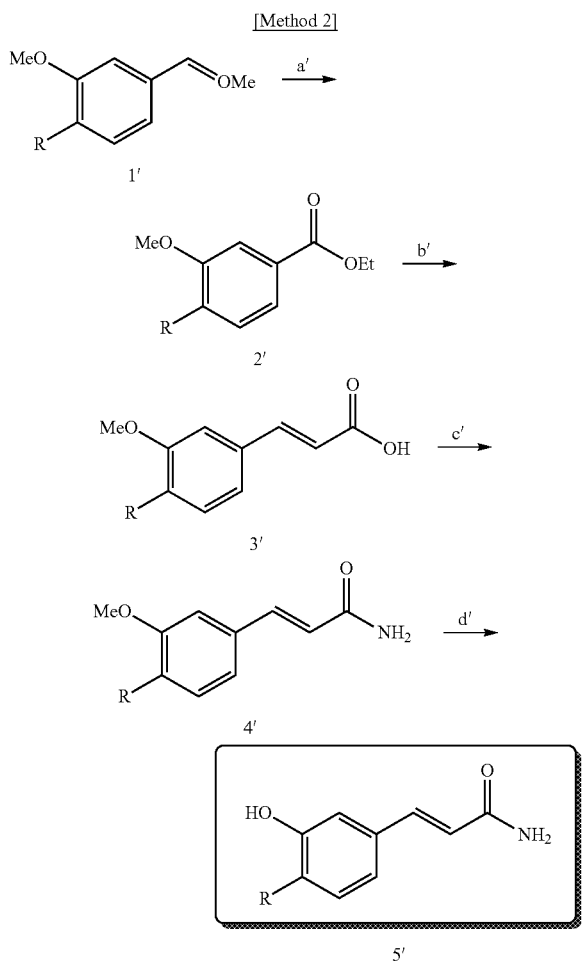

R in the Method 2 is one selected from the group consisting of —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S.

The alkyl group, alkoxy group, aryloxy, halogen, cycloalkyl and the like are as described above.

Preparation Method 3 (Method 3)

In the present invention, the following step a" is a step of preparing Compound 2 in which protection group is selectively introduced into Compound 1 using a halogenated compound under basic conditions. At this time, $K_2CO_3$, $KHCO_3$, $NaHCO_3$ and the like can be used as the base. As the reaction solvent, acetone, DMF, and the like can be used, and the reaction temperature is preferably at 40° C. to 80° C. At this time, bromobenzene, benzyl bromide, bromopropene, 2-bromopropane and the like can be used as the halogenated compound.

Step b" below is a step of preparing compound 3 by reacting compound 2 prepared in step a" with $CuBr_2$. Step b" may use acetone, DMF and the like as the reaction solvent, the reaction temperature is preferably at 40° C. to 70° C.

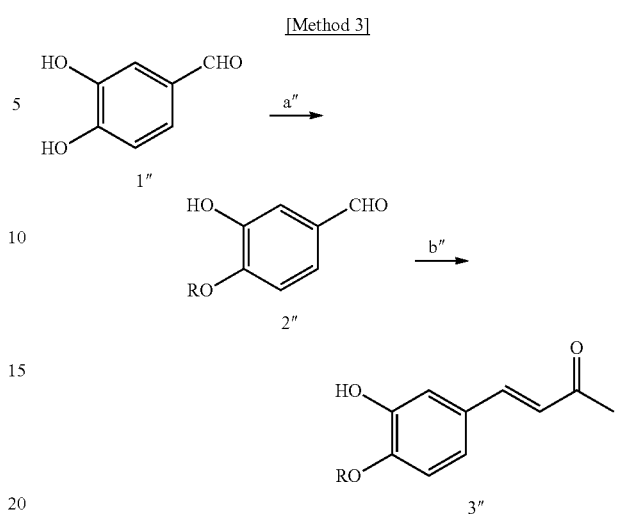

R in the Method 3 is one selected from the group consisting of $C_{1-4}$ straight or branched alkyl, $C_{1-4}$ straight or branched alkoxy, $C_{1-4}$ alkenyl, aryl group having one or more selected from the group consisting of hetero atoms and substituents, and heterocycloalkyl of 3 to 7 atoms having one or more hetero atoms, wherein the hetero atoms consist of O, N and S.

The alkyl group, alkoxy group, aryl group, halogen, cycloalkyl and the like are as described above.

The production method of the novel compounds according to the present invention is not limited to the above production method, and any other known method as well as an unknown method can be used as long as it can synthesize the compounds.

The novel compounds of the present invention prepared under the reaction solvent may be separated using concentration gradient chromatography after preparation. As the chromatography, column chromatography filled with various synthetic resins such as silica gel or activated alumina, high performance liquid chromatography (HPLC), etc. may be used alone or in combination. In an embodiment of the present invention, silica gel column chromatography and flash column chromatography were used.

In addition, the present invention provides use of a compound defined by Formula 1 above or the pharmaceutically acceptable salt thereof for preparing an agent for treating a cancer.

In addition, the present invention provides use of a compound defined by Formula 1 above or the pharmaceutically acceptable salt thereof for preparing an agent for treating a bone disease.

In addition, the present invention provides a method for treating a cancer in a subject, the method comprising administering to the subject in need thereof an effective amount of a composition comprising a compound defined by Formula 1 above or the pharmaceutically acceptable salt thereof as an active ingredient.

In addition, the present invention provides a method for treating a bone disease in a subject, the method comprising administering to the subject in need thereof an effective amount of a composition comprising a compound defined by Formula 1 above or the pharmaceutically acceptable salt thereof as an active ingredient.

As used herein, the term "effective amount" refers to, when administered to a subject, an amount that exhibits an effect of ameliorating, treating, preventing, detecting, diagnosing, or inhibiting cancer metastasis or reducing a cancer or bone disease. And the term "subject" may be an animal including a human, and may be cells, tissues, organs, etc. derived from the animal. The subject may be a patient in need of the effect.

The treatment of the present invention refers generically to ameliorating a cancer or bone disease, or a related disease thereof or a symptom of the related disease, which may include treating, substantially preventing, or ameliorating such a disease, and may include alleviating, treating or preventing a symptom or most of symptoms resulting from a cancer, bone disease or related diseases thereof, but not limited thereto.

As used herein, the term 'comprising' is used in the same way as 'containing' or 'characterized in' and does not exclude additional component elements or method steps not mentioned in the composition or method. The term 'consisting of' means to exclude additional elements, steps or components, etc., unless otherwise noted. The term "essentially consisting of" means within the scope of the composition or method, including the component elements or steps described, as well as the component elements or steps that do not substantially affect its basic properties, and the like.

Advantageous Effects

Accordingly, the present invention provides a composition for ameliorating or treating a cancer or bone disease comprising a novel compound defined by Formula 1, or a pharmaceutically acceptable salt thereof as an active ingredient and a method for preparing the same. The composition according to the present invention has low cytotoxicity to normal cells, and has a strong anti-cancer effect and strong inhibitory activity on proliferation and differentiation of osteoclasts that cause bone loss. Therefore, it can be usefully used as a therapeutic agent for cancers or bone diseases.

BRIEF DESCRIPTION OF THE DRAWINGS

FIG. 8 shows the results of measuring inhibitory effect of compounds including the compounds of the present invention, KP2 to KP8, and its positive controls, Fosamax and Osmundacetone, on osteoclast differentiation and proliferation, by TRAP assay (KP2: (E)-4-(3-hydroxy-4-methylphenyl)but-3-en-2-one, KP3: (E)-4-(4-fluoro-3-hydroxyphenyl)but-3-en-2-one, KP4: (E)-4-(4-hydroxy-3-methoxyphenyl)-3-buten-3-one, KP5: (E)-4-(3-hydroxy-4-methoxyphenyl)-3-buten-2-one, KP6: (E)-4-(3-fluoro-4-hydroxyphenyl)-3-buten-2-one, KP7: (E)-3-(3-hydroxy-4-methylphenyl)acrylamide, KP8: (E)-3-(4-fluoro-3-hydroxyphenyl)acrylamide)

MODE FOR CARRYING OUT THE INVENTION

Figure 1:
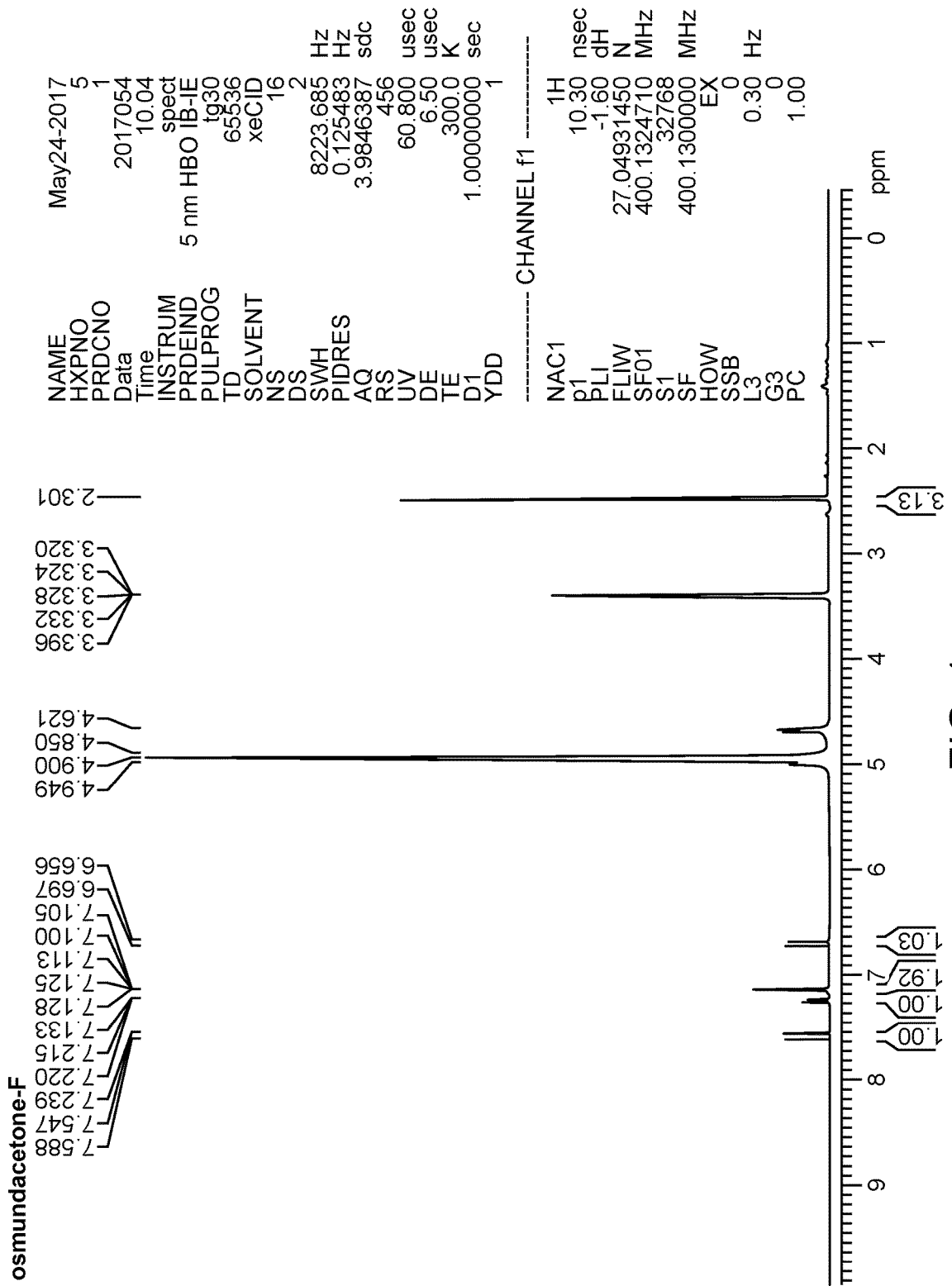
FIG. 1 shows the result of NMR identification of (E)-4-(4-fluoro-3-hydroxyphenyl)but-3-en-2-one synthesized in Example 1-1.

Hereinafter, the present invention will be described in detail with reference to the following examples.

However, the following examples are merely for illustrating the present invention and are not intended to limit the scope of the present invention.

Example 1

Synthesis of Novel Compounds

In order to identify substances having anticancer activity and inhibitory effect on osteoclast differentiation, compounds were isolated and purified from the synthetic mixture of each compound, and the chemical structure of each compound was determined by nuclear magnetic resonance (NMR) and mass spectrometry (MS).

Synthesis method of each compound and specific NMR and MS analysis results are as follows:

Example 1-1

Synthesis of (E)-4-(4-fluoro-3-hydroxyphenyl)but-3-en-2-one (KP3)

TABLE 1

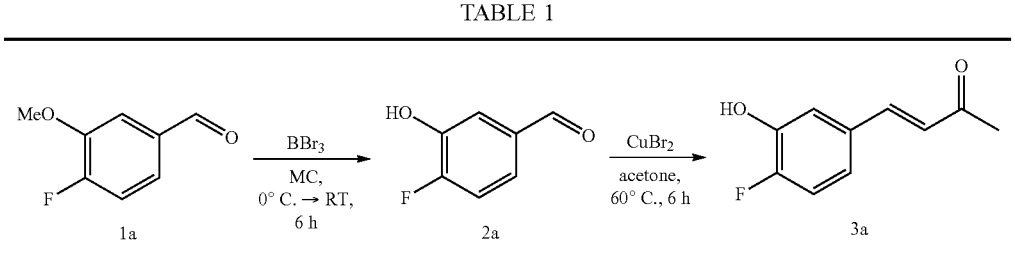

Boron tribromide (1M methylene chloride solution, 10 mL) was gradually added dropwise to a methylene chloride (10 mL) solution of 3-methoxy-4-fluorobenzaldehyde (1a) (440 mg, 2.85 mmol) under ice-cooling. The reaction solution was agitated at room temperature for 5 hours after the dropping ended. The reaction solution was again cooled with ice, iced water was gradually added to the reaction solution to terminate the reaction, and further 5N hydrochloride solution was added until the pH reached 1. After condensing the reaction solution under reduced pressure, water and ethyl acetate were added to the residue, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:n-hexane-ethyl acetate 4:1), and 210 mg of 4-fluoro-3-hydroxybenzaldehyde (2a) was obtained.

4-fluoro-3-hydroxybenzaldehyde (2a) (140.11 mg, 1.0 mmol) and $CuBr_2$ (223.35 mg, 1 mmol) in a pressured tube were dissolved in 5 mL acetone at room temperature. The reaction mixture was stirred at 60° C. After 6 h the mixture was cooled to room temperature, and filtered with Celite. The organic layer concentrated in vacuo, and product (E)-4-(4-fluoro-3-hydroxyphenyl)but-3-en-2-one (3a, 12%) as a brown solid was purified by flash chromatography using ethyl acetate and n-hexane (1:4) as an eluent.

The results of NMR and MS are as follow (See, FIG. 1):
$^1$H NMR (400 MHz, $CD_3OD$): δ 7.56 (1H, d, J=16.4 Hz), 7.22 (1H, dd, J=7.6, 2.1 Hz), 7.13-7.10 (2H, m), 6.67 (1H, J=16.4 Hz), 2.38 (3H, s); Ms(ESI) m/z: 181.1 [M+H]$^+$;

Example 1-2

Synthesis of (E)-4-(3-hydroxy-4-methylphenyl)but-3-en-2-one (KP2)

TABLE 2

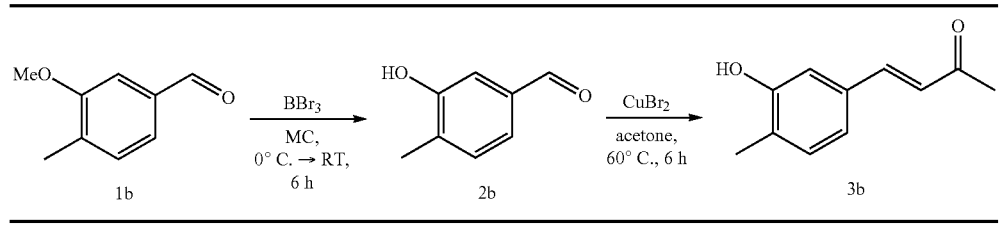

Boron tribromide (1M methylene chloride solution, 5 mL) was gradually added dropwise to a methylene chloride (5 mL) solution of 3-methoxy-4-methylbenzaldehyde (1b) (400 mg, 2.66 mmol) under ice-cooling. The reaction solution was agitated at room temperature for 5 hours after the dropping ended.

The reaction solution was again cooled with ice, iced water was gradually added to the reaction solution to terminate the reaction, and further 5N hydrochloride solution was added until the pH reached 1. After condensing the reaction solution under reduced pressure, water and ethyl acetate were added to the residue, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:n-hexane-ethyl acetate 4:1), and 150 mg (41.4%) of 3-hydroxy-4-methylbenzaldehyde (2b) was obtained.

3-hydroxy-4-methylbenzaldehyde (2b) (136.1 mg, 1.0 mmol) and $CuBr_2$ (223.35 mg, 1 mmol) in a pressured tube were dissolved in 5 mL acetone at room temperature. The reaction mixture was stirred at 60° C. After 6 h the mixture was cooled to room temperature, and filtered with Celite. The organic layer concentrated in vacuo, and product (E)-4-(3-hydroxy-4-methylphenyl)but-3-en-2-one 30 mg (3b, 17%) as a brown solid was purified by flash chromatography using ethyl acetate and n-hexane (1:4) as an eluent.

Figure 2:
FIG. 2 shows the result of NMR identification of (E)-4-(3-hydroxy-4-methylphenyl)but-3-en-2-one synthesized in Example 1-2.

The results of NMR and MS are as follow (See, FIG. 2):
$^1$H NMR (700 MHz, $CD_3OD$): δ 7.56 (1H, d, J=16.24 Hz), 7.14 (1H, d, J=7.42 Hz), 7.03-7.02 (2H, m), 6.67 (1H, J=16.24 Hz), 2.38 (3H, s), 2.22 (3H, s); Ms(ESI) m/z: 177.1 [M+H]$^+$;

Example 1-3

Synthesis of (E)-3-(3-hydroxy-4-methylphenyl)acrylamide (KP7)

TABLE 3

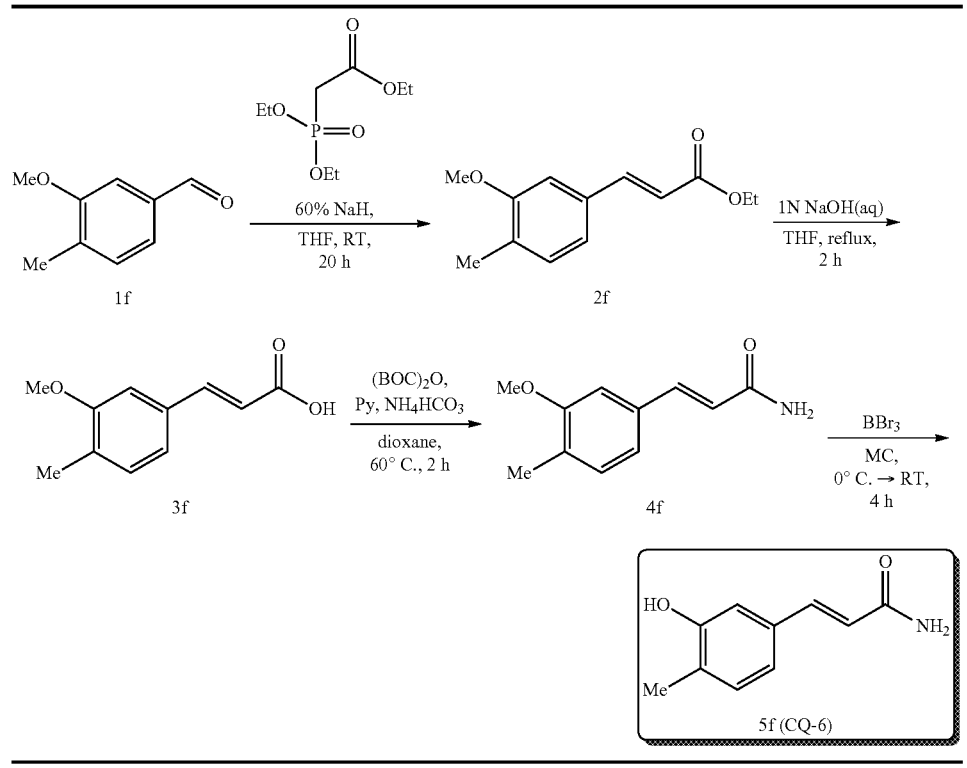

Step 1: Preparation of ethyl (E)-3-(3-methoxy-4-methylphenyl)acrylate

Sodium hydride (60% dispersion oil prewashed in hexane, 300 mg, 7.5 mmol) was stirred in dry THF (10 mL) under an atmosphere of nitrogen. Triethyl phosphonoacetate (1.345 g, 6 mmol) in dry THF (3 mL) was added dropwise and stirred for 25 minutes. Then 3-methoxy-4-methylbenzaldehyde (1f, 751 mg, 5 mmol) in THF (3 mL) was added dropwise over a period of approximately 30 minutes.

The resulting solution was stirred for 20 hours at room temperature. The reaction mixture was then quenched with water (100 mL) and was extracted with ethyl acetate (3×100 mL). The combined organic extracts were dried over magnesium sulfate, filtered and concentrated in vacuo. Purification by flash column chromatography (ethyl acetate/n-hexane 1:4) afforded unsaturated ester (2f, 700 mg, 63%) as a yellow oil.

Step 2: Preparation of (E)-3-(3-methoxy-4-methylphenyl)acrylic acid ethyl (E)-3-(3-methoxy-4-methylphenyl)acrylate (2f, 220 mg, 1 mmol) dissolved in THF (5 mL) was added dropwise to sodium hydroxide (2.0 M, 5 mL) and heated to reflux for 2 hours. The mixture was quenched with water (10 mL) and acidified to pH 2 with hydrochloric acid (2.0 M). The solution was then extracted with ethyl acetate (3×100 mL), dried over sodium sulfate, filtered and concentrated in vacuo to yield (190 mg, 98.8%) as a white solid.

Step 3: Preparation of (E)-3-(3-methoxy-4-methylphenyl)acrylamide

To a solution of (E)-3-(3-methoxy-4-methylphenyl)acrylic acid (3f, 100 mg, 0.52 mmol) and pyridine (0.1 mL) in dioxane (1 mL) was added di-tert-butyl dicarbonate (227 mg, 1.04 mmol) in one portion followed by ammonium bicarbonate (83 mg, 1.04 mmol) in one portion and the mixture was stirred at 60° C. for 2 hours.

The reaction mixture was concentrated in vacuo and the residue was partitioned between ethyl acetate and water. The ethyl acetate phase was washed with 5% aqueous sodium bicarbonate, 0.1 N HCl and brine. The organic phase was dried over sodium sulfate, filtered and concentrated in vacuo to (4f, 68 mg, 68.3%) as a yellow solid, used without further purification.

Step 4: Preparation of (E)-3-(3-hydroxy-4-methylphenyl)acrylamide

Boron tribromide (1M methylene chloride solution, 5 mL) was gradually added dropwise to a methylene chloride (1 mL) solution of (E)-3-(3-methoxy-4-methylphenyl)acrylamide (4f, 40 mg, 0.21 mmol) under ice-cooling. The reaction solution was agitated at room temperature for 4 hours after the dropping ended.

The reaction solution was again cooled with ice, iced water was gradually added to the reaction solution to terminate the reaction, and further 5N hydrochloride solution was added until the pH reached 1. After condensing the reaction solution under reduced pressure, water and ethyl acetate were added to the residue, and the organic layer was separated. The obtained organic layer was washed with a saturated sodium chloride solution, and the solvent was evaporated under reduced pressure after dried over anhydrous magnesium sulfate. The obtained residue was purified by silica gel column chromatography (elution solvent:methylene chloride-MeOH 20:1), and product (E)-3-(3-hydroxy-4-methylphenyl)acrylamide 5f (18 mg, 48.3%) as a yellow solid.

Figure 3:
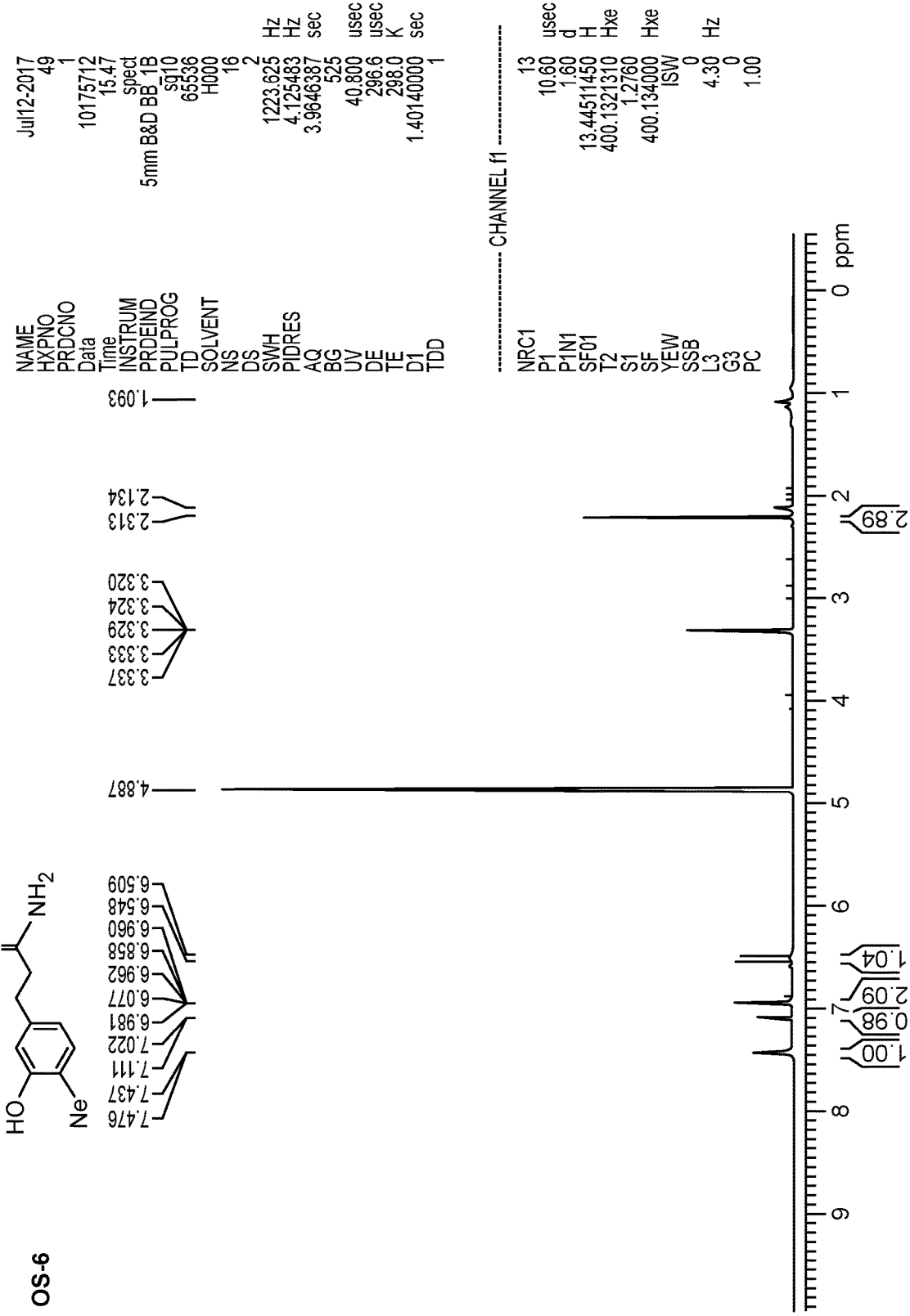
FIG. 3 shows the result of NMR identification of (E)-3-(3-hydroxy-4-methylphenyl)acrylamide synthesized in Example 1-3.

The results of NMR and MS are as follow (See, FIG. 3):

$^1$H NMR (400 MHz, MeOD): δ 7.45 (1H, d, J=15.6 Hz), 7.10 (1H, d, J=7.6 Hz), 6.98-6.95 (2H, m), 6.53 (1H, J=15.6 Hz), 2.13 (3H, s); Ms(ESI) m/z: 178.1 [M+H]$^+$;

Example 1-4: Synthesis of (E)-3-(4-fluoro-3-hydroxyphenyl)acrylamide (KP8)

TABLE 4

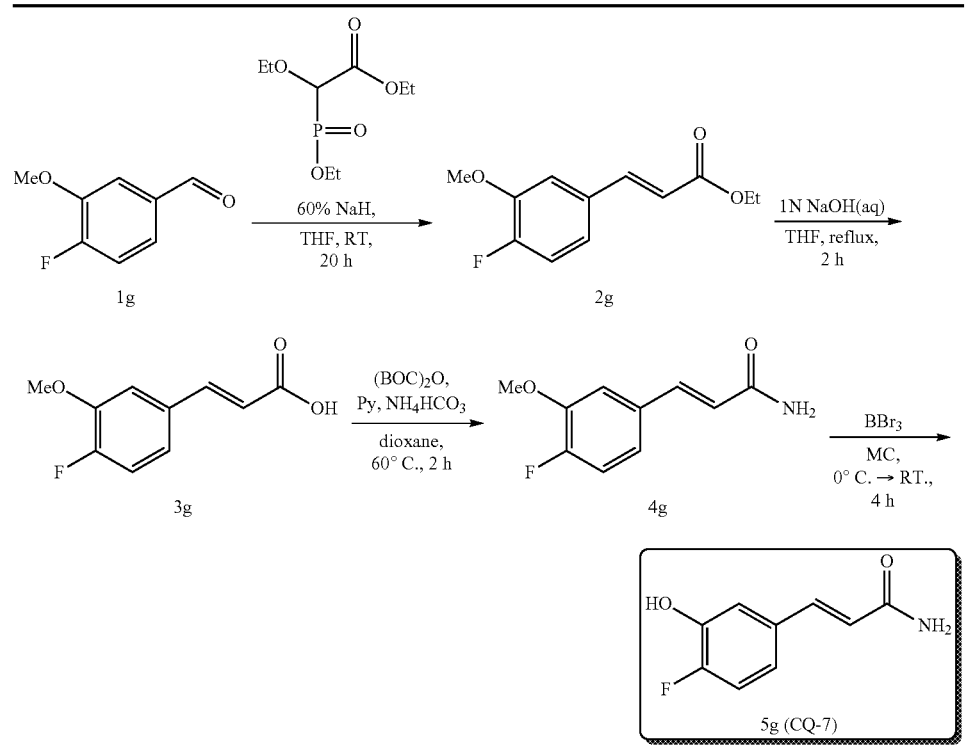

By using 3-methoxy-4-fluorobenzaldehyde (1g) instead of 3-methoxy-4-methylbenzaldehyde in Step 1 of Example 1-3, yellow compound (E)-3-(4-fluoro-3-hydroxyphenyl)acrylamide (5g, 16 mg, 40%) was obtained in the same manner as Step 3 of Example 1-3.

Specifically, 2g (680 mg, 60.6%) of yellow oil was obtained from 1g, 3g (183 mg, 93.2%) of white solid was obtained from 2g, and 4g (53 mg, 53.2%) of yellow solid was obtained from 3g, and 4g of novel compound (E)-3-(4-fluoro-3-hydroxyphenyl)acrylamide (5g, 16 mg, 40%) was obtained.

Figure 4:
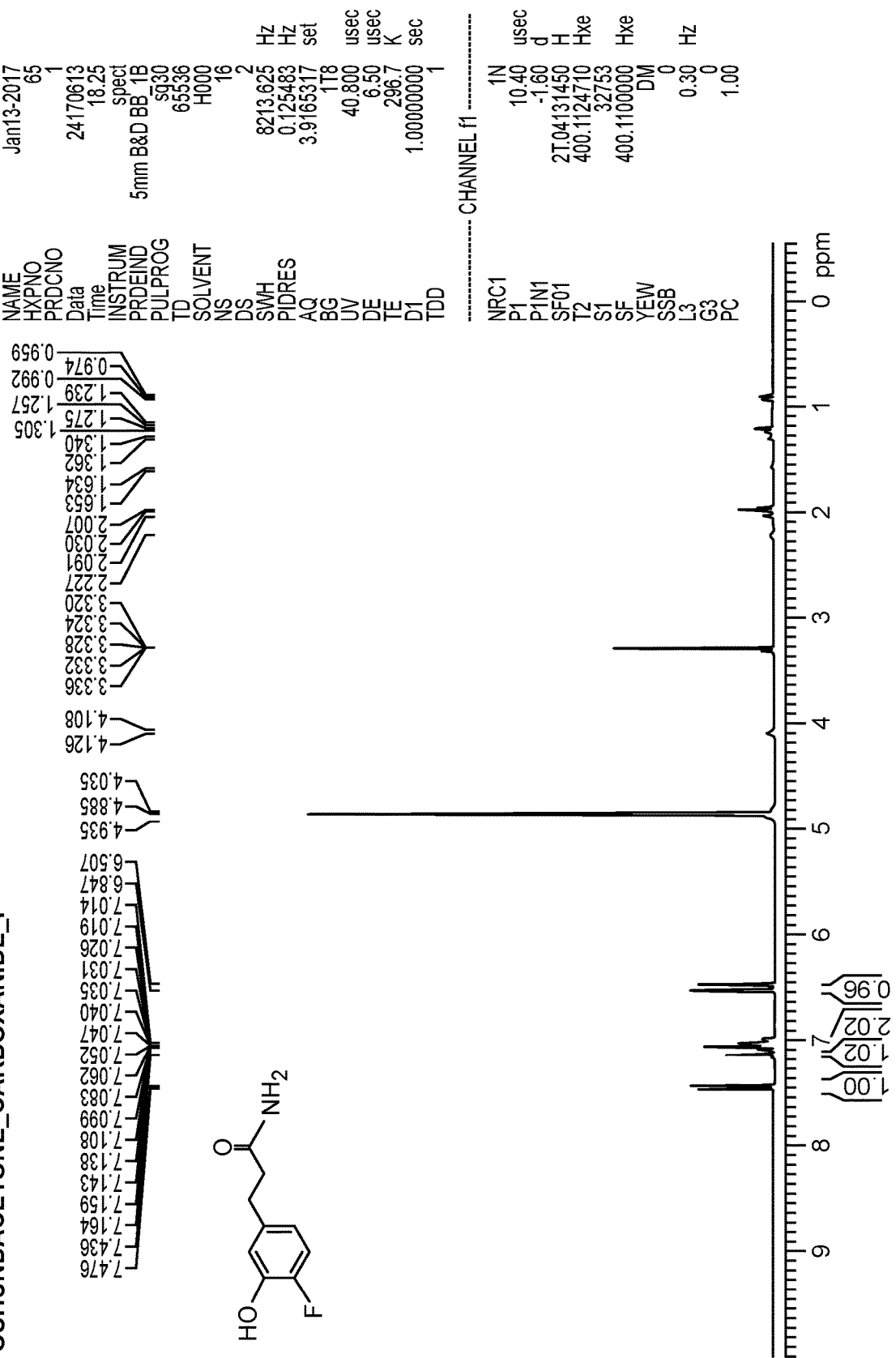
FIG. 4 shows the result of NMR identification of (E)-3-(4-fluoro-3-hydroxyphenyl)acrylamide synthesized in Example 1-4.

The results of NMR and MS are as follow (See, FIG. 4):
$^1$H NMR (400 MHz, MeOD): δ 7.45 (1H, d, J=12.4 Hz), 7.15 (1H, dd, J=2.0, 2.0 Hz), 7.10-7.01 (2H, m), 6.52 (1H, d, J=16.0 Hz); Ms(ESI) m/z: 193.1 [M+H]$^+$ Example 1-5: Synthesis of (E)-4-(3-hydroxy-4-isopropoxyphenyl)but-3-en-2-one

TABLE 5

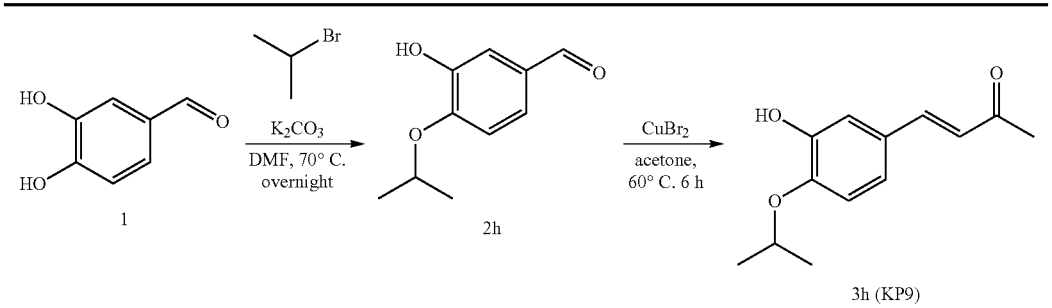

Step 1: Preparation of 3-hydroxy-4-isopropoxybenzaldehyde

A stirred suspension of 3,4-dihydrobenzaldehyde (250 mg, 1.81 mmol) and anhydrous potassium carbonate (250 mg, 1.81 mmol) in dry dimethylformamide (3 ml) was heated to 70° C. and 2-bromopropane (0.17 ml, 1.81 mmol) added dropwise under nitrogen during 30 min. The mixture was stirred for overnight at room temperature and then poured into ice water (50 ml). The aqueous mixture was extracted with ethyl acetate, and the combined extracts were washed with water, brine, and evaporated under vacuum to give a brown oil. The obtained residue was purified by silica gel column chromatography (ethyl acetate/n-hexane 1:4), and product (2h, 46 mg, 50%) as a brown solid.

Step 2: Preparation of (E)-4-(3-hydroxy-4-isopropoxyphenyl)but-3-en-2-one 3-hydroxy-4-isopropoxybenzaldehyde (2h) (50 mg, 0.277 mmol) and CuBr$_2$ (62 mg, 0.277 mmol) in a pressured tube were dissolved in 3 mL acetone at room temperature. The reaction mixture was stirred at 60° C. After 6 h the mixture was cooled to room temperature, and filtered with Celite. The organic layer concentrated in vacuo, and product (E)-4-(3-hydroxy-4-isopropoxyphenyl)but-3-en-2-one 33 mg (3h, 53.3%) as a white solid was purified by flash chromatography using ethyl acetate and n-hexane (1:4) as an eluent.

Figure 5:
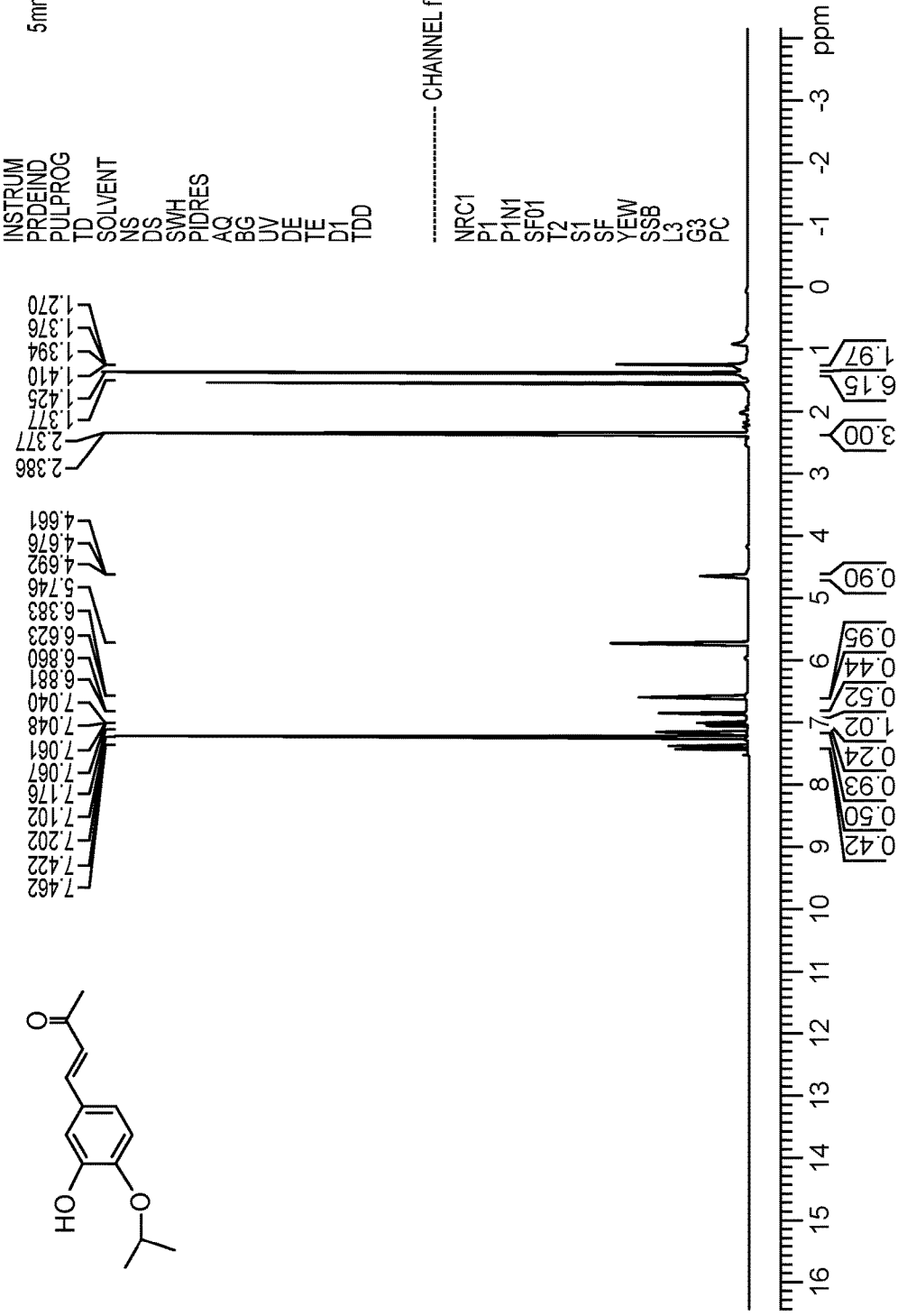
FIG. 5 shows the result of NMR identification of (E)-4-(3-hydroxy-4-isopropoxyphenyl)but-3-en-2-one synthesized in Example 1-5.

The results of NMR and MS are as follow (See, FIG. 5):
$^1$H NMR (400 MHz, CDCl$_3$) δ 7.44 (1H, d, J=16.0 Hz), 7.17 (1H, d, J=2.4 Hz), 7.05 (1H, dd, J=8.4 Hz, 6.0 Hz), 6.87 (1H, d, J=8.4 Hz), 6.60 (1H, d, J=16.0 Hz), 5.74 (1H, s), 4.67 (1H, hept, J=6.4 Hz), 2.37 (3H, s), 1.41 (6H, d, J=6.0 Hz)); Ms(ESI) m/z: 221.1 [M+H]$^+$

Example 1-6

Synthesis of (E)-4-(4-(benzyloxy)-3-hydroxyphenyl)but-3-en-2-one

TABLE 6

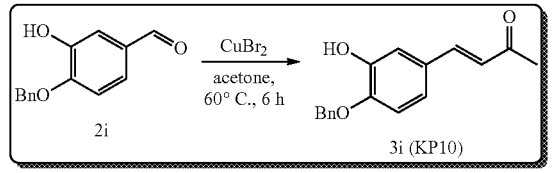

4-(benzyloxy)-3-hydroxybenzaldehyde as the target compound (2i) was obtained by the same method as in Example 1-5, using benzyl bromide instead of 2-bromopropane in Step 1 of Example 1-5.

4-(benzyloxy)-3-hydroxybenzaldehyde (2i, 50 mg, 0.22 mmol) and CuBr$_2$ (48.9 mg, 0.22 mmol) in a pressured tube were dissolved in 3 mL acetone at room temperature. The reaction mixture was stirred at 60° C. After 6 h the mixture was cooled to room temperature, and filtered with Celite. The organic layer concentrated in vacuo, and product (E)-4-(4-(benzyloxy)-3-hydroxyphenyl)but-3-en-2-one (3i, 37 mg, 62.6%) as a white solid was purified by flash chromatography using ethyl acetate and n-hexane (1:4) as an eluent.

Figure 6:
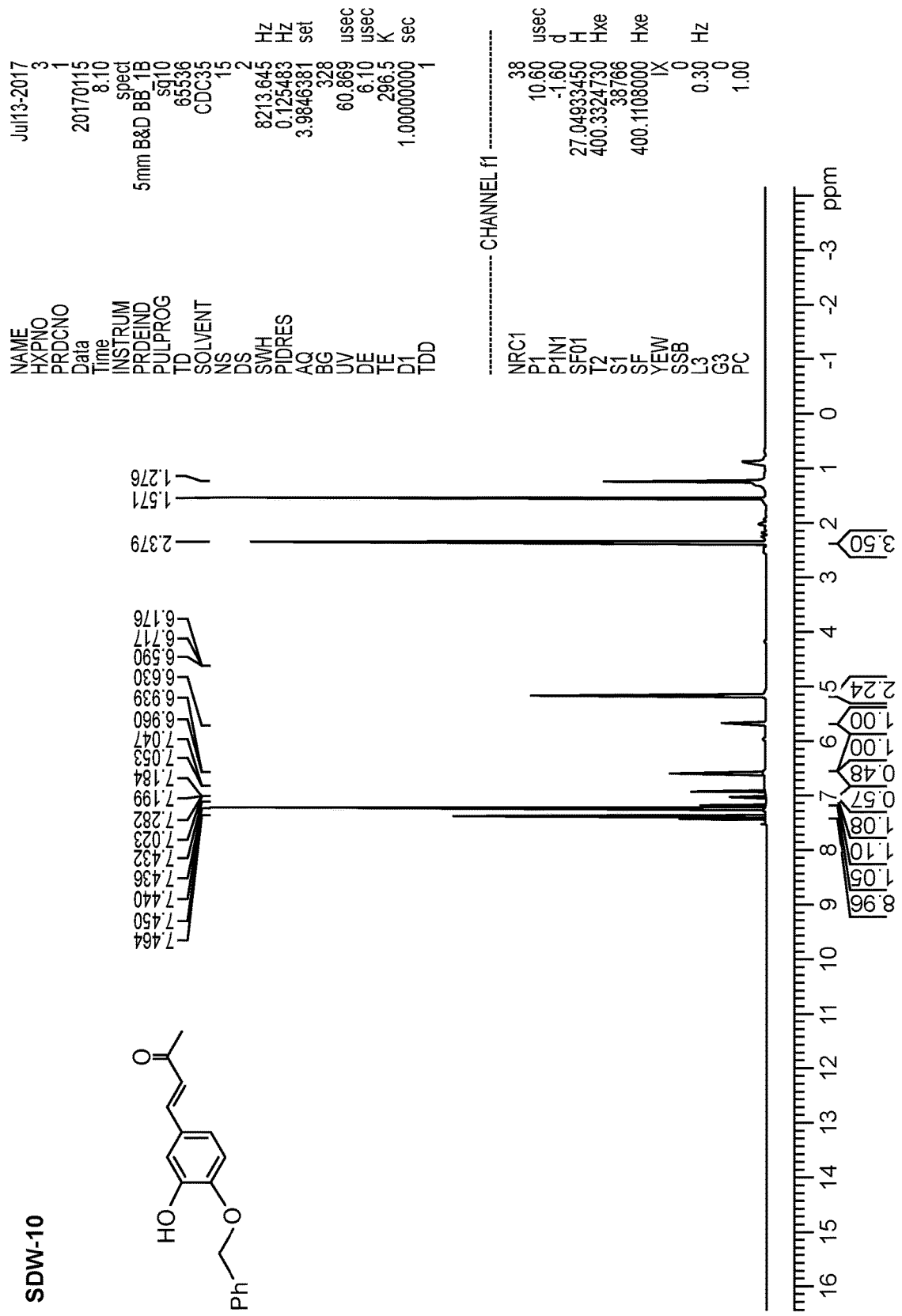
FIG. 6 shows the result of NMR identification of (E)-4-(4-benzyloxy-3-hydroxyphenyl)but-3-en-2-one synthesized in Example 1-6.

The results of NMR and MS are as follow (See, FIG. 6):
$^1$H NMR (400 MHz, CDCl$_3$) δ 7.46-7.42 (6H, m), 7.19 (1H, d, J=2.0 Hz), 7.05 (1H, dd, J=8.4 Hz, 2.4 Hz), 6.95 (1H, d, J=8.4 Hz), 6.95 (1H, d, J=8.4 Hz), 6.61 (1H, d, J=16.0 Hz), 5.71 (1H, s), 5.17 (2H, s), 2.37 (3H, s); Ms(ESI) m/z: 269.2 [M+H]$^+$

Example 1-7

Synthesis of (E)-4-(4-(allyloxy)-3-hydroxyphenyl)but-3-en-2-one

TABLE 7

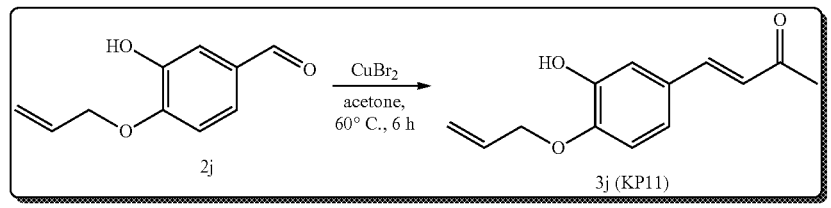

4-(allyloxy)-3-hydroxybenzaldehyde as the target compound (2j) was obtained by the same method as in Example 1-5, using bromopropene instead of 2-bromopropane in Step 1 of Example 1-5.

4-(allyloxy)-3-hydroxybenzaldehyde (2j, 50 mg, 0.28 mmol) and CuBr$_2$ (62.7 mg, 0.28 mmol) in a pressured tube were dissolved in 3 mL acetone at room temperature. The reaction mixture was stirred at 60° C. After 6 h the mixture was cooled to room temperature, and filtered with Celite. The organic layer concentrated in vacuo, and product (E)-4-(4-(allyloxy)-3-hydroxyphenyl)but-3-en-2-one (3j, 34 mg, 55.6%) as a white solid was purified by flash chromatography using ethyl acetate and n-hexane (1:4).

Figure 7:
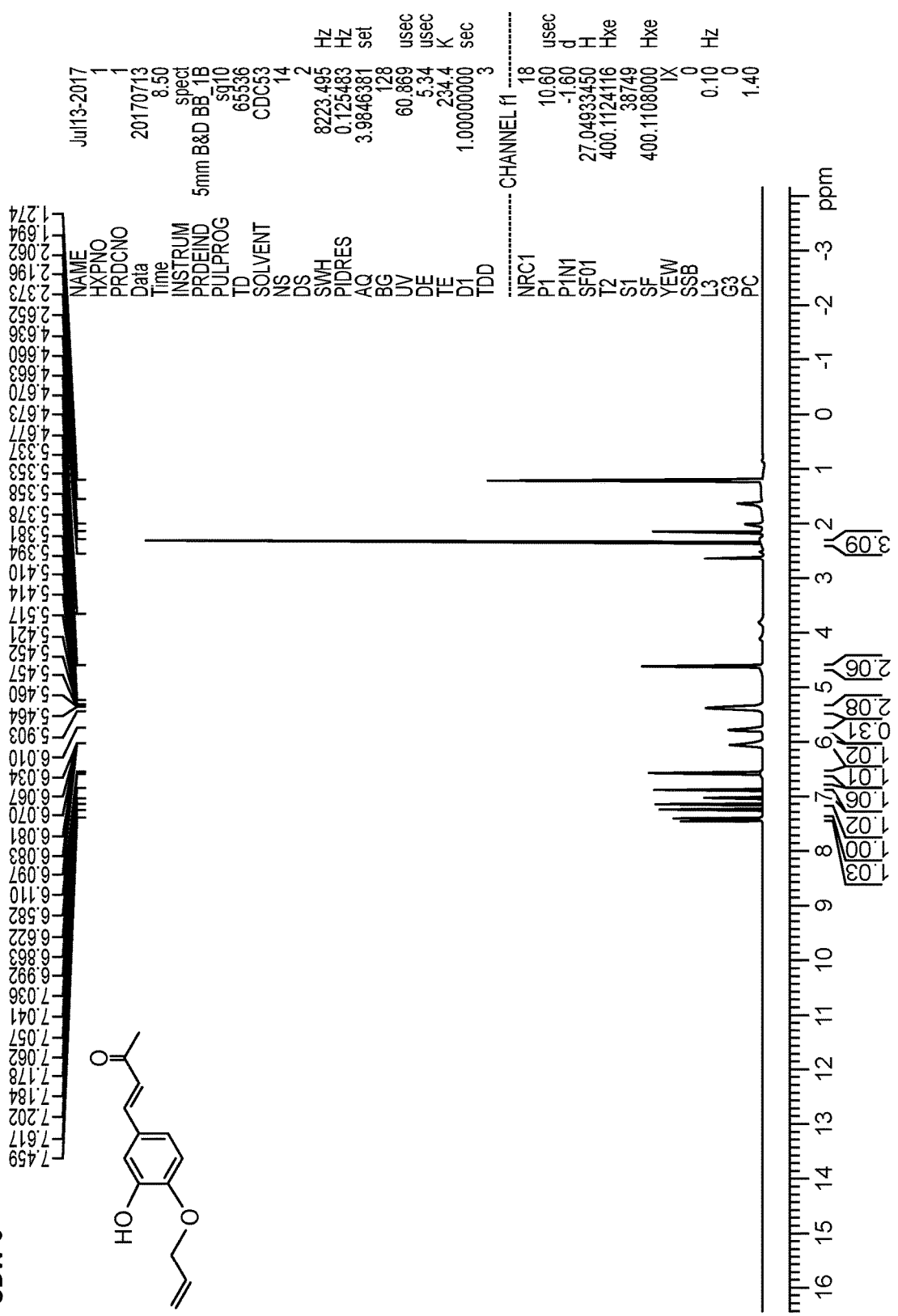
FIG. 7 shows the result of NMR identification of (E)-4-(4-allyloxy-3-hydroxyphenyl)but-3-en-2-one synthesized in Example 1-7.

The results of NMR and MS are as follow (See, FIG. 7):
$^1$H NMR (400 MHz, CDCl$_3$) δ 7.43 (1H, d, J=16.4 Hz), 7.18 (1H, d, J=2.4 Hz), 7.04 (1H, dd, J=8.4 Hz, 2.0 Hz), 6.87 (1H, d, J=8.0 Hz), 6.60 (1H, d, J=16.0 Hz), 6.11-6.04 (1H, m), 5.80 (1H, s), 5.43 (1H, dd, J=17.2 Hz, 12.8 Hz), 5.36 (1H, dd, J=10.4 Hz, 8.0 Hz), 4.67-4.65 (2H, m), 2.37 (3H, s); Ms(ESI) m/z: 219.2 [M+H]$^+$;

Example 2

MTT Assay

The cytotoxicity against normal cells and cancer cells was confirmed using the MTT assay for the novel compounds KP2 to KP8 prepared in Example 1.

MTT assay method is as follows:

Normal cells (RAW264.7 rat macrophage cell line (osteoblast progenitor cell) and NIH3T3 mouse fibroblast line) and cancer cells (AGS human gastric cancer cell line, A549 human lung cancer cell line, HepG2 human liver cancer cell line, HCT116 human colon cancer cell line, PC3 human prostate cancer Cell line, Caki-1 human kidney cancer cell line, T24 human bladder cancer cell line, HT1080 human fibrosarcoma cell line, B16F10 mouse melanoma cell line) were cultured in 5% CO2 in 96-well plates containing DMEM with 10% FBS (fetal bovine serum). After incubation, KP2 to KP8 and controls (osmundacetone and 4-hydroxybenzalacetone) were added to the cell medium and incubated for 48 hours. Thereafter, 100 μl of MTT (0.5 mg/mL phosphate buffered saline) was added, followed by incubation for 2 hours. 100 μl of DMSO was added to each well, followed by incubation for 10 minutes, and the absorbance was measured at 550 nm using a microplate reader (SPCTRA MAX 340PC, Molecular Devices, USA). Absorbance is calculated by the formula below as an indicator of the number of cells that survived, and reproducibility was confirmed by three experiments.

The rate of cell proliferation (%)=OD550(sample)/OD550(control)

TABLE 8

| | The compounds of Formula 1 |
|---|---|
| KP2 | 4-(3-Hydroxy-4-methylphenyl)-3-buten-2-one |
| KP3 | 4-(4-fluoro-3-hydroxyphenyl)-3-buten-2-one |
| KP4 | 4-(4-hydroxy-3-methoxyphenyl)-3-buten-2-one |
| KP5 | 4-(3-Hydroxy-4-methoxyphenyl)-3-buten-2-one |
| KP6 | 4-(3-Fluoro-4-hydroxyphenyl)-3-buten-2-one |
| KP7 | 4-(3-Hydroxy-4-methylphenyl)acrylamide |
| KP8 | 4-(4-fluoro-3-hydroxyphenyl)acrylamide |

TABLE 9

The result of MTT assay for normal cells with the compoumds

| | $LD_{50}$ (μM) Normal cells | |
|---|---|---|
| Compound | RAW264.7 | NTH3T3 |
| Osmundacetone | 529 ± 41 | >5000 |
| 4-Hydroxybenzalacetone | 294 ± 45 | 201 ± 10 |
| KP2 | 395 ± 22 | 688 ± 12 |
| KP3 | 503 ± 57 | >5000 |
| KP4 | 399 ± 42 | >5000 |
| KP5 | 261 ± 79 | >5000 |
| KP6 | 1110 ± 48 | >5000 |
| KP7 | >5000 | >5000 |
| KP8 | >5000 | >5000 |

As can be seen in Table 9, the LD50 for normal cells calculated based on the change in cell proliferation rate after administration of KP2 to KP8 was similar to that of Osmundacetone's LD50. Only KP2 showed weak cytotoxicity. In the macrophage cell line RAW264.7, KP2 to KP5 showed weak cytotoxicity, suggesting that these compounds have weak immunosuppressive functions. Therefore, it can be seen that the compounds of the present invention having low cytotoxicity to normal cells as a whole can be safely used in pharmaceutical and food compositions.

TABLE 10

The result of MTT assay for cancer cells with the compounds

| | $LD_{63}$ (μM) Cancer cell | | | | | | | | |
|---|---|---|---|---|---|---|---|---|---|
| Compound | AGS | A549 | HepG2 | HCT116 | PC3 | Caki-1 | T24 | HT1080 | H16F10 |
| Osmundacetone | 56.1 ± 2.1 | >5000 | >5000 | 689 ± 27 | 60.6 ± 14 | 695 ± 14 | 2000 ± 250 | >5000 | 64.9 ± 59 |
| KP2 | 209 ± 5.9 | 471 ± 24 | 339 ± 79 | 380 ± 32 | 309 ± 3.1 | 387 ± 57 | 1120 ± 67 | 256 ± 14 | 298 ± 27 |
| KP3 | 239 ± 14 | 1090 ± 46 | 612 ± 95 | 389 ± 18 | 387 ± 48 | 408 ± 12 | >5,000 | 379 ± 10 | 278 ± 15 |
| KP4 | 417 ± 15 | 3010 ± 38 | — | 495 ± 13 | 223 ± 85 | 506 ± 13 | >5,000 | >5,000 | 423 ± 39 |
| KP5 | 181 ± 15 | 1890 ± 210 | — | 491 ± 72 | 291 ± 5.7 | 409 ± 11 | >5000 | 381 ± 49 | 441 ± 58 |
| KP6 | 336 ± 3.9 | 901 ± 28 | — | 490 ± 38 | 205 ± 13 | 449 ± 40 | 3610 ± 130 | >5,000 | 421 ± 41 |
| KP7 | 329 ± 14 | 989 ± 50 | 379 ± 38 | 315 ± 19 | 394 ± 140 | 361 ± 16 | 1040 ± 360 | 309 ± 10 | 1210 ± 110 |
| KP8 | 569 ± 4.8 | 935 ± 10 | 1280 ± 390 | >5,000 | >5,000 | 2990 ± 58 | 203 ± 69 | 1090 ± 19 | >5,000 |

As can be seen in Table 10, the LD50 of the cancer cells of the compound calculated based on the change in cell proliferation rate after administration of KP2 to KP8 showed stronger anticancer activity in some cancers compared to the LD50 of Osmundacetone.

Specifically, for A549 lung cancer cells, KP2 showed significantly better cancer cell inhibitory activity than Osmundacetone, and in HepG2 hepatocellular carcinoma cells, KP2 and KP7 showed significantly better cancer cell inhibitory activity, and in HP116 colorectal cancer cells, it was confirmed that KP2, KP3 and KP7 showed 2 times better inhibitory activity than Osmundacetone except for KP8. All other compounds except KP8 in Caki-1 kidney cancer cells were found to have superior inhibitory activity than Osmundacetone. In T24 bladder cancer cells, KP8 showed particularly better inhibitory activity. Finally, the inhibitory activity of the compounds except KP80 on HT1080 fibrosarcoma cancer cells were all superior to Osmundacetone, a positive control.

Therefore, it was confirmed that the inhibitory activity of the compounds of the present invention on lung cancer, colorectal cancer, kidney cancer, bladder cancer, and fibrosarcoma cancer cells was much better than or similar to that of Osmundacetone, and thus the compounds of the present invention can be usefully used as anticancer agents.

Example 3

Inhibitory Activity Against Proliferation and Differentiation of Osteoclast

For the compounds prepared in Example 1, the inhibitory activity against proliferation and differentiation of osteoclast was confirmed by using a osteoclast specific staining method, TRAP assay (tartrate-resistant acid phosphatase).

The specific method of the TRAP assay is as follows:

1. Bone Marrow Cell Culture

The tibia and femur were aseptically excised from 6 to 8 weeks old male C57BL/6 mice, and bone marrow cells were collected aseptically with a syringe (21G, Korea Green Cross). Bone marrow cells were suspended in 500 µl of -MEM medium (Gibco BRL Co.) containing sodium bicarbonate (2.0 g/L), streptomycin (100 mg/L) and penicillin (100,000 units/mL), and aliquoted into a 48-well plate, and assay was carried out with triplicate. The progenitor cells of osteoclasts, monocytes, were isolated and treated with RANKL and M-CSF, which are differentiation promoters, to differentiate into osteoclasts within 5-7 days.

2. Measurement of Osteoclast Differentiation

1) Sample preparation: KP2 to KP8 (0.5 µM, 1 µM, 5 µM or 10 µM), Fosamax (0.5 µM, 1 µM, 5 µM, or 10 µM) and the like were dissolved in DMSO (dimethylsulfoxide) or sterile distilled water at appropriate concentrations, respectively. Compounds were prepared in the same manner as in Example 1.

2) Sample administration: The Samples were continuously administered to the medium at 1:20 (v/v; 25 µL of sample per 500 µL of medium) from the first day of culture of bone marrow cells, and the medium was replaced at 3 days intervals.

3) Osteoclast differentiation measurement: Osteoclasts were defined as TRAP-positive multinucleated cells stained with TRAP. TRAP staining solution was prepared by dissolving 5 mg of naphthol AS-MS phosphate (Sigma N-4875) and 25 mg of Fast Red Violet LB salt as a coloring reagent in about 0.5 mL of N,N-dimethylformamide, and then mixing with 0.1N NaHCO$_3$ buffer solution (50 mL) containing 50 mM tartaric acid. The reaction reagents were stored in the refrigerator until use.

Bone marrow cells were cultured in a medium containing differentiation factors for 6-7 days, and then the medium was removed, washed with PBS, and fixed in PBS containing 10% formalin for 2-5 minutes. After fixed for 1 minute with a 1:1 mixture of ethanol and acetone, and dried. The fixed cells were treated with TRAP staining solution for 60 minutes at 37° C. with light blocking, washed with PBS, and then stained with Hematoxylin.

Among the TRAP-positive cells in the microscope field, cells with two or more nuclei were determined as osteoclasts and the number of cells was measured. The osteoclast differentiation inhibitory activity of the compound was calculated by IC50, 50% inhibitory concentration compared to the control.

As can be seen in FIG. 8, the groups treated with KP2 to KP8 compound not only significantly inhibited the formation of giant osteoclasts, multinucleated cells, similar to the positive control groups (groups added with Osmundacetone or Fosamax to the culture medium), but also, in the case of KP2, the IC50 value was about three times better than the group added with Osmundacetone. In the case of KP5, IC50=1 µM showed strong osteoclast inhibitory activity, that is about 40 times of Fsamax (IC50=4 µM), the most widely used therapeutic agent for osteoporosis, and 80 times of osmundacetone (IC50=8 µM). In addition, the proliferation of osteoclast progenitor cells was also significantly suppressed, and the effect of inhibiting proliferation as well as the differentiation of osteoclasts was also found to be significant.

Example 4

Effect on Proliferation and Differentiation of Osteoblast

Effect of KP4 to KP6 on proliferation and differentiation of osteoblast were confirmed using ALP (Alkaline phosphatase) assay, a method for measuring osteoblast activity.

Alkaline phosphatase (ALP), which is present in the cell membranes of osteoblasts, is known as a marker of osteoblast activity and is a regulator of inorganic phosphate transport, cell division or differentiation during calcification. Therefore, ALP activity was measured to determine the effect of the compounds of the present invention on the activity of osteoblasts. ALP activity was indirectly calculated by measuring the amount of p-nitrophenol, which is produced from hydrolysis of p-nitrophenyl phosphate (pNPP, Sigma, St. Louis, Mo., USA) in which ALP act as a catalyst, using a microplate reader at 405 nm wavelength.

Specifically, osteoblasts (mouse MC3T3-E1) were aliquoted into a 96-well plate ($3 \times 10^3$ cells/100 µL/well) with α-MEM medium containing ascorbic acid (50 µg/mL) and 10 mM β-glycerophosphate, a differentiation factors of osteoblast. Then, KP4 to KP6 of the present invention, and osmundacetone were added at a final concentration of 10 µM and 50 µM, followed by changing medium every 72 hours and incubating for 14 days. After 14 days, the culture medium was removed from each well, washed three times with PBS, lysed with 0.2% Nonidet P-40/10 mmol/L MgCl$_2$, and then treated ultrasonic wave with sosonifier cell disrupter (Model W-380, Heat Systems-Ultrasonics Inc., Farmingdale, N.Y.) for 3 minutes. The cell lysate was centrifuged at 1500 g for 10 minutes and the supernatant was collected to measure ALP activity. To account for changes in ALP activity according to cell number differences, total protein levels were measured using bicinchoninic acid (BCA) protein assay kit with bovine serum albumin as the standard protein, and enzyme activity was expressed as a percentage against the control group without the compound treatment.

As shown in Table 11, KP4 and KP5 showed higher ALP activity at 10 µM and 50 µM concentrations than the control without the treatment of compounds, especially when KP4

((E)-4-(4-hydroxy-3-methoxyphenyl)-3-buten-2-one) was added at a concentration of 50 μM, the ALP activity was increased by 400% or more compared with the control group, and it was confirmed that the osteoblast activity was increased 1.5 times compared to osmundacetone treat group. These were very good results compared to the osteoblast activators used in the treatment of osteoporosis in the existing clinical practice. On the other hand, KP6 showed good activity on inhibiting osteoclast differentiation (IC50=6 μM), but there was no activity on activating osteoblast.

TABLE 11

Measurement of ALP activity

| COMPOUNDS | % Activation of ALP activity | |
|---|---|---|
| | 10 μM | 50 μM |
| Osmundacetone | 115 ± 9.4 | 279 ± 61 |
| KP4 | 113 ± 2.9 | 422 ± 6.9 |
| KP5 | 103 ± 1.1 | 175 ± 0.3 |
| KP6 | 102 ± 0.2 | 100 ± 0.8 |

INDUSTRIAL APPLICABILITY

Since the novel compounds according to the present invention exhibit a strong inhibitory activity on proliferation and differentiation of osteoclasts that cause bone loss in addition to cancer cell specific cytotoxicity, it can be usefully used for developing safe and effective anti-cancer agents, and therapeutic agents for preventing and treating or foods for ameliorating bone diseases such as osteoporosis, and the like.

The invention claimed is:

1. A method for treating a bone cancer in a subject, the method comprising administering to the subject in need thereof an effective amount of a composition comprising a compound defined by Formula 1 below or the pharmaceutically acceptable salt thereof as an active ingredient:

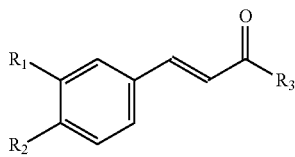

[Formula 1]

wherein, R1 and R2 are different from each other,
R1 and R2 are each independently selected from the group consisting of —H, —OH, —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S;
R3 is one selected from the group consisting of $C_{i-4}$ straight or branched alkyl, —NH$_2$, —NHR4, —N(R4)$_2$, and —OH; and
R4 is $C_{1-4}$ straight or branched alkyl,
wherein the compound defined by Formula 1 is selected from the group consisting of the following compounds;
(1) (E)-4-(4-hydroxy-3-methoxyphenyl)-3-buten-2-one;
(2) (E)-4-(3-hydroxy-4-methoxyphenyl)-3-buten-2-one; and
(3) (E)-4-(3-fluoro-4-hydroxyphenyl)-3-buten-2-one.

2. A method for treating osteoporosis in a subject, the method comprising administering to the subject in need thereof an effective amount of a composition comprising a compound defined by Formula 1 below or the pharmaceutically acceptable salt thereof as an active ingredient:

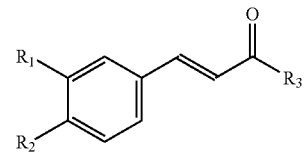

[Formula 1]

wherein, R1 and R2 are different from each other,
R1 and R2 are each independently selected from the group consisting of —H, —OH, —SH, $C_{1-4}$ straight or branched alkyl, $C_{1-4}$ straight or branched alkoxy, halogen, allyloxy, benzyloxy, aryloxy having one or more selected from the group consisting of hetero atoms and substituents, and heterocycloalkyl of 3 to 7 atoms having one or more hetero atoms, wherein the hetero atoms consist of O, N and S;
R3 is one selected from the group consisting of $C_{i-4}$ straight or branched alkyl, —NH$_2$, —NHR4, —N(R4)$_2$, and —OH; and
R4 is $C_{1-4}$ straight or branched alkyl,
wherein the compound defined by Formula 1 is selected from the group consisting of the following compounds;
(1) (E)-4-(3-hydroxy-4-methoxyphenyl)-3-buten-2-one; and
(2) (E)-4-(3-fluoro-4-hydroxyphenyl)-3-buten-2-one.

* * * * *